(12) United States Patent
Shah et al.

(10) Patent No.: US 10,888,281 B2
(45) Date of Patent: Jan. 12, 2021

(54) SYSTEM AND METHOD FOR DISEASE RISK ASSESSMENT AND TREATMENT

(71) Applicant: Percusense, LLC, Valencia, CA (US)

(72) Inventors: Rajiv Shah, Rancho Palos Verdes, CA (US); Bradley Liang, San Francisco, CA (US); Bahar Sutorius, Thousand Oaks, CA (US); Katherine Wolfe, Dunwoody, GA (US); Ellen Messer, Pasadena, CA (US); Shaun Pendo, Wofford Heights, CA (US)

(73) Assignee: PercuSense, Inc., Valencia, CA (US)

( * ) Notice: Subject to any disclaimer, the term of this patent is extended or adjusted under 35 U.S.C. 154(b) by 613 days.

(21) Appl. No.: 15/417,055

(22) Filed: Jan. 26, 2017

(65) Prior Publication Data

US 2017/0325749 A1 Nov. 16, 2017

Related U.S. Application Data

(60) Provisional application No. 62/443,070, filed on Jan. 6, 2017, provisional application No. 62/401,481, filed
(Continued)

(51) Int. Cl.
*A61B 5/05* (2006.01)
*A61B 5/00* (2006.01)
(Continued)

(52) U.S. Cl.
CPC ............ *A61B 5/7275* (2013.01); *A61B 5/076* (2013.01); *A61B 5/1459* (2013.01);
(Continued)

(58) Field of Classification Search
CPC ... A61B 5/01; A61B 5/14532; A61B 5/14542; A61B 5/14546; A61B 5/14551;
(Continued)

(56) References Cited

U.S. PATENT DOCUMENTS

| 5,724,983 A | 3/1998 | Selker et al. |
| 7,022,070 B2 | 4/2006 | Ebner et al. |

(Continued)

FOREIGN PATENT DOCUMENTS

| GB | 2533774 | 7/2016 |
| WO | 2016063084 | 4/2016 |

OTHER PUBLICATIONS

Surviving Sepsis Campaign case study, Datamonitor, Apr. 2008, Reference Code BPCS307.
(Continued)

*Primary Examiner* — Navin Natnithithadha
*Assistant Examiner* — Andrey Shostak
(74) *Attorney, Agent, or Firm* — PercuSense, Inc.

(57) ABSTRACT

An apparatus for early detection of sepsis in a host is disclosed. The apparatus includes a first sensor to directly measure a glucose level, a second sensor to directly measure a lactate level and a third sensor to directly measure a tissue oxygen level. The first sensor, the second sensor, and the third sensor all being inserted at a single point of entry in a subcutaneous space of the host such that a predetermined correlation between the glucose level, lactate level, and tissue oxygen level signals conditions related to sepsis.

14 Claims, 13 Drawing Sheets

Related U.S. Application Data on Sep. 29, 2016, provisional application No. 62/383,233, filed on Sep. 2, 2016, provisional application No. 62/370,226, filed on Aug. 2, 2016, provisional application No. 62/353,559, filed on Jun. 23, 2016, provisional application No. 62/348,806, filed on Jun. 10, 2016, provisional application No. 62/336,482, filed on May 13, 2016.

(51) Int. Cl.

| | |
|---|---|
| *A61B 5/145* | (2006.01) |
| *G16H 10/60* | (2018.01) |
| *G16H 50/30* | (2018.01) |
| *G16H 50/20* | (2018.01) |
| *G16H 40/67* | (2018.01) |
| *A61B 5/07* | (2006.01) |
| *A61B 5/1455* | (2006.01) |
| *A61B 5/1459* | (2006.01) |
| *A61B 5/1473* | (2006.01) |
| *A61B 5/01* | (2006.01) |
| *A61B 5/11* | (2006.01) |
| *A61B 5/1486* | (2006.01) |

(52) U.S. Cl.
CPC ........ *A61B 5/1473* (2013.01); *A61B 5/14532* (2013.01); *A61B 5/14542* (2013.01); *A61B 5/14546* (2013.01); *A61B 5/14551* (2013.01); *A61B 5/412* (2013.01); *A61B 5/4842* (2013.01); *A61B 5/6861* (2013.01); *G16H 10/60* (2018.01); *G16H 40/67* (2018.01); *G16H 50/20* (2018.01); *G16H 50/30* (2018.01); *A61B 5/0002* (2013.01); *A61B 5/01* (2013.01); *A61B 5/11* (2013.01); *A61B 5/14865* (2013.01); *A61B 5/746* (2013.01); *A61B 2560/0214* (2013.01); *A61B 2560/063* (2013.01); *A61B 2562/0219* (2013.01); *A61B 2562/06* (2013.01)

(58) Field of Classification Search
CPC . A61B 5/1459; A61B 5/1473; A61B 5/14865; A61B 5/412; A61B 5/482; A61B 5/6861; A61B 5/7275; G16H 50/20

See application file for complete search history.

(56) References Cited

U.S. PATENT DOCUMENTS

| | | | |
|---|---|---|---|
| 7,252,637 B2 | 8/2007 | Ebner et al. | |
| 7,450,986 B2 | 11/2008 | Nguyen et al. | |
| 7,941,199 B2 | 5/2011 | Kiani | |
| 8,016,776 B2 | 9/2011 | Bourget et al. | |
| 8,116,841 B2 | 2/2012 | Bly et al. | |
| 8,285,356 B2 | 10/2012 | Bly et al. | |
| 8,412,293 B2 | 4/2013 | Rule | |
| 8,444,578 B2 | 5/2013 | Bourget et al. | |
| 8,527,449 B2 | 9/2013 | Gajic et al. | |
| 8,663,107 B2 | 3/2014 | Kiani | |
| 8,668,644 B2 | 3/2014 | Ong et al. | |
| 8,718,752 B2 | 5/2014 | Libbus et al. | |
| 8,790,257 B2 | 7/2014 | Libbus et al. | |
| 8,795,170 B2 | 8/2014 | Pipke | |
| 8,795,174 B2 | 8/2014 | Manicka et al. | |
| 8,814,792 B2 | 8/2014 | Raptis et al. | |
| 8,818,481 B2 | 8/2014 | Bly et al. | |
| 8,920,318 B2 | 12/2014 | Inbar | |
| 8,932,220 B2 | 1/2015 | Ong et al. | |
| 8,951,193 B2 | 2/2015 | Ong et al. | |
| 9,060,722 B2 | 6/2015 | Teixeira | |
| 9,125,566 B2 | 9/2015 | Libbus et al. | |
| 9,295,429 B2 | 3/2016 | Ong et al. | |
| 9,326,720 B2 | 5/2016 | McLaughlin | |
| 9,339,195 B2 | 5/2016 | Pitruzzello et al. | |
| 10,226,576 B2* | 3/2019 | Kiani | A61B 5/0205 |
| 2003/0032871 A1 | 2/2003 | Selker et al. | |
| 2005/0065556 A1 | 3/2005 | Reghabi | |
| 2005/0119540 A1 | 6/2005 | Potts et al. | |
| 2005/0192488 A1 | 9/2005 | Bryenton | |
| 2006/0047283 A1* | 3/2006 | Evans, III | A61B 5/076 606/102 |
| 2008/0119707 A1 | 5/2008 | Stafford | |
| 2008/0176271 A1* | 7/2008 | Silver | A61B 5/0031 435/29 |
| 2009/0149724 A1 | 6/2009 | Mark et al. | |
| 2009/0156911 A1 | 6/2009 | Rule et al. | |
| 2009/0163774 A1 | 6/2009 | Thatha et al. | |
| 2010/0004517 A1 | 1/2010 | Bryenton | |
| 2010/0057490 A1 | 3/2010 | Kocis et al. | |
| 2010/0274102 A1 | 10/2010 | Teixeira | |
| 2012/0095304 A1 | 4/2012 | Biondi | |
| 2012/0136221 A1 | 5/2012 | Killen et al. | |
| 2012/0209088 A1 | 8/2012 | Romem | |
| 2013/0053655 A1 | 2/2013 | Castellanos | |
| 2013/0123592 A1 | 5/2013 | Rule | |
| 2013/0338543 A1 | 12/2013 | Gegner et al. | |
| 2014/0058218 A1 | 2/2014 | Randlov et al. | |
| 2014/0180038 A1 | 6/2014 | Kiani | |
| 2014/0275824 A1 | 9/2014 | Couse | |
| 2014/0316220 A1 | 10/2014 | Sheldon | |
| 2014/0330091 A1 | 11/2014 | Libbus et al. | |
| 2014/0330136 A1 | 11/2014 | Manicka et al. | |
| 2014/0350352 A1 | 11/2014 | Baronov et al. | |
| 2015/0005589 A1 | 1/2015 | Bly et al. | |
| 2015/0011844 A1 | 1/2015 | Paradis | |
| 2015/0025329 A1 | 1/2015 | Amarasingham et al. | |
| 2015/0141770 A1 | 5/2015 | Rastogi et al. | |
| 2015/0141771 A1 | 5/2015 | Inbar | |
| 2015/0148617 A1 | 5/2015 | Friedman | |
| 2015/0164434 A1 | 6/2015 | Noury et al. | |
| 2015/0272494 A1 | 10/2015 | Fuerst | |
| 2015/0342538 A1 | 12/2015 | St Pierre et al. | |
| 2016/0135755 A1 | 5/2016 | Lu et al. | |
| 2016/0143596 A1 | 5/2016 | Bhattacharya et al. | |
| 2016/0174913 A1 | 6/2016 | Somanath et al. | |
| 2016/0192848 A1 | 7/2016 | Ravishankar et al. | |
| 2016/0220127 A1 | 8/2016 | Boyer | |

OTHER PUBLICATIONS

E Abraham, Mervyn Singer, Mechanisms of Sepsis-Induced Organ Dysfunction and Recovery, Aug. 27, 2007, Springer Science & Business Media, Leipzig, Germany. Library of Congress Control No. 2006929196.

P.R. Moret, J. Weber, J.-CL. Haissly, H. Denolin, Lactate Physiologic, Methodologic and Pathologic Approach, 1980, Springer, Berlin, Heidelberg. Online ISBN: 978-3-642-67525-6.

C.A. Burtis, M.M. Muller, Advances in Critical Care Testing—The 2002 IFCC—Roche Diagnostics Award, 2004, Springer-Verlag Berlin Heidelberg New York. ISBN 978-3-540-40752-2.

A. Gullo, Anaesthesia, Pain, Intensive Care and Emergency—A.P.I.C.E Proceedings of the 22nd Postgraduate Course in Critical Care Medicine, Venice-Mestre, Italy—Nov. 9-11, 2007, 2008 Springer-Verlag Italia. Library of Congress Control No. 2007939172.

Fisher, Amy P., "Screening for Sepsis: A Key Strategy for Early Identification and Management of Septic Patients" (2014). DNP Practice Inquiry Projects. Paper 31.

Novosad SA, Sapiano MR, Grigg C, et al. Vital Signs: Epidemiology of Sepsis: Prevalence of Health Care Factors and Opportunities for Prevention. MMWR Morb Mortal Wkly Rep 2016;65:864-869. DOI: http://dx.doi.org/10.15585/mmwr.mm6533e1.

Epstein L, Dantes R, Magill S, Fiore A. Varying Estimates of Sepsis Mortality Using Death Certificates and Administrative Codes—United States, 1999-2014. MMWR Morb Mortal Wkly Rep 2016;65:342-345. DOI: http://dx. doi.org/10.15585/mmwr.mm6513a2.

(56) References Cited

OTHER PUBLICATIONS

Sutton J, Freidman B. Trends in Septicemia Hospitalizations and Readmissions in Selected HCUP States, 2005 and 2010. HCUP Statistical Brief #161. Sep. 2013. Agency for Healthcare Research and Quality, Rockville, MD.
Angus, Derek C; Van Der Poll, Tom, Severe Sepsis and Septic Shock, The New England Journal of Medicine, Aug. 29, 2013, 840-851.
Hanazaki, Kazuhiro, Blood glucose control in patients with severe sepsis and septic shock, World Journal of Gastroenterology, Sep. 7, 2009, 15(33) 41332-4136.
Mervyn Singer, The role of mitochondrial dysfunction in sepsis-induced multi-organ failure, 2014, Virulence, 5:1, 66-72, DOI: 10.4161/viru.26907.
Sharad Manaktala, Stephen R. Claypool, Evaluating the impact of a computerized surveillance algorithm and decision support system on sepsis mortality, J Am Med Inform Assoc 2017; 24 (1):88-95. doi: 10.1093/jamia/ocw056.

\* cited by examiner

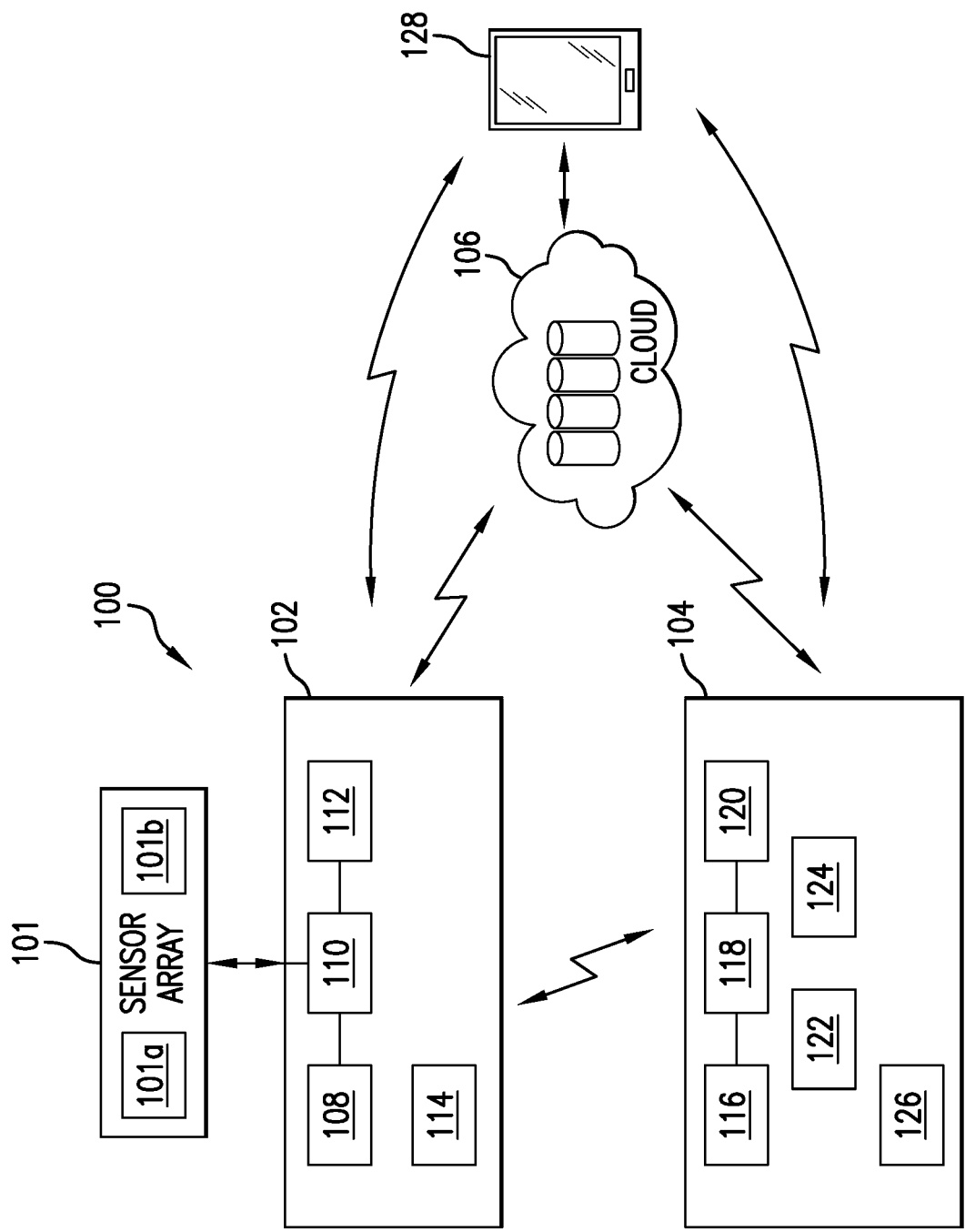

| Risk Metric | Relative Weight Triage Mode no diabetes | Relative Weight Triage mode with diabetes |
|---|---|---|
| Glucose | 1 | 0 |
| Glucose predicted | 0.5 | 0 |
| Glucose percent out of range | 0 | 0 |
| Lactate | 3 | 2 |
| Lactate rate of change | 1 | 0.5 |
| pO2 | 2 | 2 |
| pO2 rate of change | 0.5 | 0.5 |
| Temperature | 3 | 3 |
| Edema detection | 1.5 | 1.5 |
| Lactate/Glucose | 0.25 | 0 |
| Glucose/Oxygen | 0.25 | 0 |
| Lactate/Oxygen | 0.5 | 0.5 |
| Autoimmune disorder baseline risk | 0 | 3 |

FIG. 6

| Risk Metric | Triage | Monitoring mode | Remote monitoring | Custom mode |
|---|---|---|---|---|
| glucose | 1 | 2 | 1 | Physician defined |
| glucose (predicted) | 0.5 | 1 | 0 | Physician defined |
| glucose % out of range | 0 | 0 | 0.5 | Physician defined |
| lactate | 3 | 2 | 3 | Physician defined |
| lactate rate of change | 1 | 1 | 1 | Physician defined |
| pO2 | 2 | 2 | 2 | Physician defined |
| pO2 rate of change | 0.5 | 1 | 0.5 | Physician defined |
| temperature | 3 | 3 | 3 | Physician defined |
| Edema detection | 1.5 | 1.5 | 1.5 | Physician defined |
| lactate/glucose | 0.25 | 0 | 0.25 | Physician defined |
| glucose/oxygen | 0.25 | 0 | 0.25 | Physician defined |
| lactate/oxygen | 0.5 | 0 | 0.5 | Physician defined |

FIG. 7

SYSTEM AND METHOD FOR DISEASE RISK ASSESSMENT AND TREATMENT

RELATED APPLICATIONS

This application claims the benefit of U.S. provisional application Nos. 62/336,482, filed May 13, 2016; 62/348,806, filed Jun. 10, 2016; 62/353,559, filed Jun. 23, 2016; 62/370,226, filed Aug. 2, 2016; 62/383,233, filed Sep. 2, 2016; 62/401,481, filed Sep. 29, 2016; and 62/443,070 filed Jan. 6, 2017. The applications listed above are hereby incorporated by reference in their entireties for all purposes.

FIELD OF THE INVENTION

The invention generally relates to systems and methods for real time metabolic monitoring to enable diagnosis and monitoring of disease progression including risk assessment, diagnosis, treatment and monitoring of sepsis. More specifically, the invention relates to the use of sensors and related electronics in conjunction with algorithms and software for the early identification and warning before the onset of sepsis.

BACKGROUND OF THE INVENTION

Sepsis is a medical condition that is the result of a severe inflammatory response to a circulation infection. Current estimates suggest that approximately one-million Americans will develop sepsis on an annual basis and between 30 and 50 percent of those patients will succumb due to sepsis related complications such as multi-organ failure. The economic burden of sepsis is significant with recent estimates suggesting yearly in patient costs well in excess of $22 billion.

The economic burden of sepsis is expected to increase dramatically in the coming years given the increasing prevalence and incidence of sepsis due in large part to both increased life expectancy and an increase in antibiotic resistant bacteria. The costs associated with treating sepsis are significant in part due to the intensive care unit (ICU) as being the primary venue for highly invasive early goal directed treatment (EGDT) strategies that use the output of centrally placed catheters capable of measuring arterial pressure in comparison to a goal to modify or modulate the use of intravenous fluids, oxygen, drugs and blood transfusions in what can be a futile fight for survival. Those who recover from a sepsis infection may never actually completely recover, resulting in large indirect costs associated with sepsis recovery that further burdens an already burdened healthcare system.

A randomized control trial (RCT) published in 2001 showed via a single-site, EGDT administration of a hemodynamic driven protocol for six hours following diagnosis and triage resulted in a reduction of in-hospital mortality from 46.5% to 30.5% and evolved into the standard of care and has been included in the six-hour sepsis bundle protocol used by many hospitals. A larger RCT named Protocol Care for Early Septic Shock (ProCESS) sought to replicate the previously discussed results within a larger population enrolled across a large number of diverse academic hospital emergency departments. The ProCESS trial demonstrated no improvement in 60-day survival rates between the EGDT and normal care cohort. Interestingly, the overall mortality rate within all cohorts of the ProCESS clinical trial group was approximately 21% (~30% at 90 days), which was substantially lower than in hospital mortality rate documented in the previous study thereby suggesting improvements in nominal sepsis related care.

A study similar to ProCESS named Protocolized Management in Sepsis (ProMISe) conducted in the United Kingdom showed no difference in the survival at 90 days between the EGDT and control group. The 90-day mortality rate associated with the ProMISe group was approximately 29%, a number quite similar to that observed during the ProCESS trial. The results associated with the two recently run large clinical trials strongly suggest little incremental benefit associated with current approaches to EGDT; however, the high mortality rates (~30%) at 90 days suggest a critical need for better therapeutic protocols.

Of note in both the ProCESS and ProMISe trials is the high level of admission lactate concentration associated with the baseline or admission blood sample analysis. Average lactate concentration for the two study populations was 2.5-3.5× a high normal level of 2 mM. Fuller and Dellinger have proposed that lactate and lactate clearance be used instead of, or in conjunction with, mixed venous oxygen saturation as an endpoint in any quantitative or goal directed resuscitation protocol applied to critical illness such as sepsis. Their review of the literature strongly suggests that therapeutic interventions that successfully drive lactate clearance is directly related to reduced mortality.

The claimed invention seeks to address timely and cost effective methods and systems to diagnose sepsis. In many examples discussed below multiple analytes and physical parameters are monitored. In other examples, diagnosis is based on monitoring multiple analytes without physical parameters. While embodiments and examples may be related to particular analytes and physical parameters, the scope of the disclosure and claims should not be construed to be limited to the specifically addressed analytes and parameters. Rather it should be recognized that additional or other analytes and physical parameters can be monitored to assist in the detection and diagnosis of sepsis.

BRIEF SUMMARY OF THE INVENTION

In one embodiment a system to enable risk assessment of the onset of sepsis is disclosed. The system includes a sensor array for insertion within subcutaneous tissue for continuous monitoring of at least two analytes that are indicators of the onset of sepsis. Further included within the system is an electronics module that includes a power supply, a processor, memory, and a bi-directional communications module. In one embodiment the electronics module is configured to couple with the sensor array while a power supply powers the sensor array and a processor is in communication with the sensor array. The processor calculates a risk index for the onset of sepsis based on characteristics of the at least two analytes being continuously monitored. The risk index being transmitted to and stored on a computer readable electronic health record.

In another embodiment, an apparatus for early detection of sepsis in a host is disclosed. The apparatus includes a first sensor to directly measure a glucose level, a second sensor to directly measure a lactate level and a third sensor to directly measure a tissue oxygen level. The first sensor, the second sensor, and the third sensor all being inserted at a single point of entry in a subcutaneous space of the host such that a predetermined correlation between the glucose level, lactate level, and tissue oxygen level signals conditions related to sepsis.

In still another embodiment, a method for the early detection of sepsis in a host is disclosed. The method includes an operation that inserts via a single point of entry a sensor assembly having a first sensor, a second sensor and a third sensor into subcutaneous tissue of the host. The method continues with an operation to measure a glucose level using the first sensor. An additional operation measures a lactate level using the second sensor, while still an additional operation measures tissue oxygen level using the third sensor. A subsequent operation determines a risk index for sepsis based on predetermined correlations between the glucose level, the lactate level and the tissue oxygen level.

In another embodiment, a method for the early detection of cancer is disclosed. The method includes a first operation of inserting a sensor assembly having a first sensor and a second sensor via a single point of entry into subcutaneous tissue. Other operations measure a first analyte level with the first sensor and a second analyte level with the second sensor. The second analyte being different than the first analyte. The method further determines a risk index for cancer based on predetermined correlations between the levels of the first analyte and second analyte. Wherein the first analyte and second analyte are selected from a group consisting of glucose, lactate, oxygen or a ketone.

Another embodiment discloses a method to monitor for a medical condition that includes an operation that identifies at least two different biological markers relevant to the pathophysiological process of the medical condition. A later operation enables at least two sensors to measure the at least two identified biological markers. A later operation configures the sensors onto a sensor array that is applied at a single site and another operation monitors the biological markers for pathophysiological conditions indicative of development of the medical condition.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

FIG. 1A is an exemplary block diagram showing components within a system to determine a risk score of developing sepsis, in accordance with embodiments of the invention.

FIG. 3A-1 is an exemplary hybrid flowchart and block diagram illustrating operations and elements used to perform an operation that evaluates data to determine a risk score, in accordance with embodiments of the invention.

FIG. 3A-2 is an exemplary hybrid flowchart and block diagram further including the application of conditional logic or conditional weights, in accordance with embodiments of the invention.

FIG. 5 includes a table of exemplary triage mode relative weight coefficients for patients with and without diabetes, in accordance with embodiments of the invention.

FIG. 6 includes a table of exemplary relative weighting coefficients for particular metrics, in accordance with embodiments of the invention.

DETAILED DESCRIPTION

Figures 1, 1B:
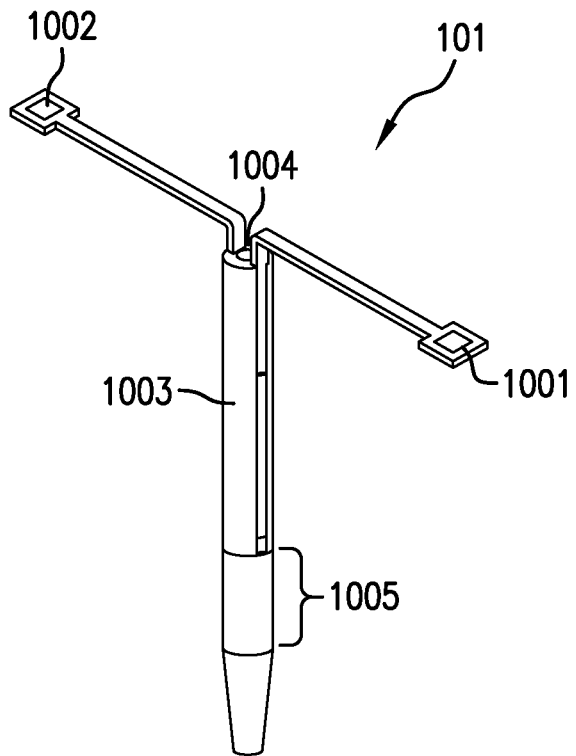
FIGS. 1B-1 and 1B-2 are exemplary isometric views of sensor array 101, in accordance with embodiments of the invention.

Simultaneous continuous or periodic measurement of physical parameters and chemical entities as a means of measuring disease progression or inflection that requires timely clinical intervention can be extended to a multitude of disease states and may include multiple measurement modalities. The design of such medical monitoring systems requires an understanding of the pathophysiological processes associated with a particular illness or disease. From this basic understanding, a number of small molecules, biological markers of disease, and physiological measures with high diagnostic and prognostic value for a particular disease and/or condition can be identified. Sensors that rely on physical, electrochemical, and optical transducers can be functionalized to directly or indirectly measure the small molecules, biological markers, and physiological measures associated with a specific disease. Advanced manufacturing techniques can then be used to integrate the sensors in question into a multi-analyte or multi-parameter that can be deployed invasively or noninvasively within a target population. Software algorithms that combine an understanding of disease, artificial intelligence, and machine learning can be embedded in the instrumentation or systems that power and acquires data from a disease specific multi-parameter sensor to assess the cellular and/or systemic progression of condition or disease. Configurable alerts and alarms associated with the medical monitoring system can be communicated through wired and wireless methods to enable timely therapeutic intervention in order to derive the benefits of proactive disease or illness management.

Disclosed below is a robust system that performs real-time simultaneous continuous monitoring of specific risk metrics to generate a risk score for developing sepsis. The risk score for developing sepsis is determined using risk metrics based on data obtained from (i) sensors placed implanted within or associated with a subject and/or (ii) other external input available on the subject (such as electronic medical records, test data from hospital/clinic measurements where the subject is being evaluated, or has been evaluated previously, for a medical condition). Risk metrics based on sensor data can be based on continuous and substantially real-time monitoring of analytes and physiological parameters relevant to sepsis. In one embodiment, the risk metrics includes, but is not limited to analytes such as, glucose, tissue oxygen and lactate. Detectable changes in those risk metrics can be indicative of a localized infection progressing towards sepsis. For example, the pathophysiological processes of a localized infection developing into sepsis and the relationship between glucose, lactate and tissue oxygen is described below. As a localized infection initially begins progressing toward sepsis there can be a rapid increase in insulin resistance that results in a measurable increase in glucose. Undetected and untreated the infection can continue to progress towards sepsis where the measureable increase in glucose eventually begins coinciding with a measureable decrease in tissue oxygen. Further progression toward sepsis results in decreased tissue oxygen coinciding with an increase in lactate levels and highly elevated lactate level, in conjunction with other factors, can be indicative of a septic infection. Accordingly, analysis of continuous real time measurements of glucose, lactate and tissue oxygen in light of the pathophysiological process described above enables determination of a risk score of developing sepsis.

In a simple embodiment the risk score is determined based on a sum of normalized primary inputs, where primary inputs are sensor measured concentrations of analytes such as, but not limited to, glucose, tissue oxygen and lactate. A more refined risk score is determined by incorporating secondary inputs, which are risk metrics that are calculated based on primary inputs. Examples of secondary inputs include, but are not limited to rates of change of glucose, tissue oxygen and lactate. In a variation of this embodiment, the risk score additionally incorporates looking at measured inputs over time differently. For example, rather than using the same time window for all evaluations, each analyte or metric is examined at a preferred frequency. Relative weighting factors can also be applied to either or both primary and secondary inputs to emphasize or deemphasize particular risk metrics when determining a risk score. Sources for relative weighting are found in personal health records such in measured or calculated metrics or be derived from personal health records. An example of relative weighting derived from measured metrics includes, but is not limited to decreasing the influence of high lactate concentrations when coincident with nominal lactate clearance rates. An example of relative weighting derived from personal health records is increasing weighting for all metrics when a subject is immunocompromised.

The system is configurable for use in a variety of environments including, but not limited to triage, patient monitoring and remote monitoring, where each mode may be further supplemented with a feedback/treatment mode. In a triage environment the system determines a risk score that can help determine if a patient may have developed sepsis. In a patient monitoring environment, the risk score and changes to the risk score over time enables both automated evaluation if a patient may be trending toward developing sepsis and automated evaluation of efficacy of therapy for patients known to be septic. In a remote monitoring environment, the risk score enables monitoring of patients for early warning signs indicative of the onset of sepsis.

Within the triage environment the system is applied to a patient entering a medical facility such as, but not limited to an emergency room, an urgent care clinic or a mobile medical emergency environment such as an ambulance or helicopter. Other alternative triage environments include locations with elevated numbers of high risk individuals such as elder care facilities, nursing homes and hospice facilities. In triage environments the system is intended to rapidly determine a risk score for sepsis based on risk metrics that are indicative of an existing sepsis condition. This enables initiation of goal directed therapy for the treatment of sepsis within a minimal amount of time.

If a patient is found to be septic, the system is capable of transitioning from a diagnostic tool to a monitoring device capable of providing data to assist in evaluating the efficacy of ongoing therapy. Assuming a triage patient is deemed to not be septic, the system can transition to a patient monitoring mode where the objective is to output a risk score that provides notification that a patient is trending toward conditions indicative of sepsis.

Applied within a patient monitoring environment, the system enables monitoring of septic patients, continued analysis of data from triage patients and further includes monitoring of postoperative patients. In many embodiments the patient monitoring environment is an ambulatory patient within a medical care facility such as a hospital or an outpatient clinic. Regardless of the type of facility, for patients afflicted with sepsis, the system can provide real time continuous monitoring of analytes that are indicative of the efficacy of ongoing therapy. The real time continuous data can enable more frequent and responsive changes in goal directed therapy. For example, rather than having to wait for discrete lactate samples to be returned from a laboratory, with real time continuous monitoring physicians can easily see if lactate levels are increasing or decreasing and additionally the rate at which lactate levels are changing. With rate of change data, physicians can change and modify treatment protocols and see the results of previous changes more rapidly than with discrete samples that may take hours to return from the laboratory.

For patients without sepsis the system continues to generate a risk score for developing sepsis with the objective of providing notification that a patient may be trending toward conditions indicative of sepsis. When the system provides notification a patient is trending towards a condition indicative of sepsis various care protocols may require increased monitoring of the patient. Alternatively, updated care protocols may proscribe early intervention and application of goal directed therapy to halt further trending towards sepsis that minimize the likelihood of the patient continuing to trend toward sepsis.

In a remote monitoring environment, the system can further be transitioned from a medical care facility to a mobile monitor capable of operating as a home monitor or any other location outside of a medical care facility. Use of the system as a mobile monitor may be desirable for patients being discharged from a medical facility that may be considered high risk to develop sepsis such as an elderly postoperative patient. In another embodiment, the remote monitoring capability of the system can be expanded to generally high risk individuals such as those with compromised immune systems, and those living in elder care, nursing homes or hospice facilities.

The goal for remote monitoring is to provide early notification that a patient is trending toward a condition indicative of sepsis. In many of these embodiments it may not be desirable to monitor lactate while scrupulously monitoring rates of change of glucose and oxygen. In some embodiments of remote monitoring, the notification is provided to the patient while in other embodiments the notification is provided to an attending physician. In still other embodiments, notification is provided to both the patient and at least one medical or care professionals such as, but not limited to an attending physician, nurse, resident healthcare provider, or a centralized care facility that can contact EMS. Similar to patient monitoring use of the system as a remote monitor can result in a patient seeking more timely application of goal directed therapy that containing an infection to a localized system and minimizes the likelihood of the infection becoming systemic.

Optionally enhancing each of the previously described modes for the system is feedback/treatment mode. Feedback mode is intended to monitor the effects of any treatment protocol and provide real-time, actionable information to external control algorithms whose aim is to optimize the management of therapy delivery to subjects with sepsis or a high risk of developing sepsis. In many embodiments, this is accomplished by modifying therapy based on system outputs achieving targets and/or set points for specific risk metrics based on a specific clinical protocol.

FIG. 1A is an exemplary block diagram showing components within a system 100 to determine a risk score of developing sepsis, in accordance with embodiments of the invention. Broadly, the system 100 includes a sensor array 101 that includes analytes sensors 101a and physical sensors 101b powered by an electronics module 102 that further enables bi-directional communication with a plurality of remote devices, such as, but not limited to an external monitor 104, cloud computing systems 106 and mobile devices 128. The remote devices enable different aspects of functionality of the system 100, such as, but not limited to entry of patient specific data, display of historical and trending data acquired by the system 100, and machine learning. The totality of components shown in FIG. 1A enable the system 100 to be used across a variety of environments such as triage, patient monitoring and remote monitoring. However, embodiments tailored for a specific environment may not include all of the components shown in FIG. 1A. For example, use of the system 100 as a remote monitor in a home may not utilize an external monitor 104. Likewise, when the system 100 is used as a patient monitor in a hospital environment, the system 100 may not include a mobile device 128. The inclusion of all of the components within FIG. 1A is intended to illustrate the flexibility and adaptability of the system 100 to be used in different environments. However, regardless of environment, an element of the system 100 that is required for all embodiments is the sensor array 101.

Sensor Array

Figures 1, 1B, 2:
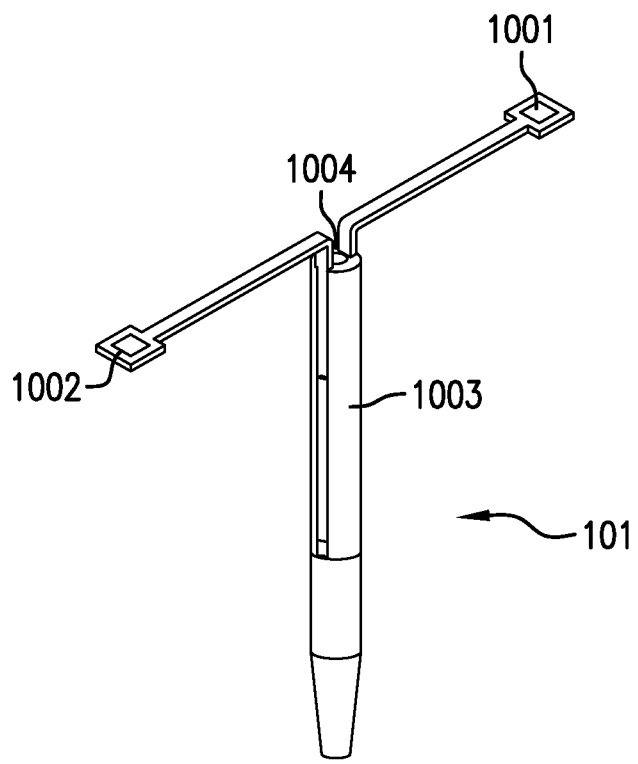

FIGS. 1B-1 and 1B-2 are exemplary isometric views of sensor array 101, in accordance with embodiments of the invention. At a minimum, the sensor array 101 includes a plurality of analyte sensors such as, but not limited to sensors configured to continuously measure glucose, lactate and oxygen or combinations thereof. The respective analyte sensors are formed either first sensor assembly 1001 or second sensor assembly 1002 that are placed or coupled with a sensor carrier 1003. Sensor carrier 1003 includes area 1005 that is configurable to receive physical sensors, such as, but not limited to thermometers, accelerometers and the like. Insertion hollow 1004 running through the sensor carrier 1003 enables insertion of the sensor array 101 via a single point of entry using an insertion sharp such as, but not limited to a needle. After insertion of the sensor array 101 the insertion sharp is withdrawn leaving insertion hollow 1004 empty. The insertion hollow 1004 can optionally be utilized to place additional physical sensors within the subject such as, but not limited to a discrete tissue fluid monitoring sensor, e.g. a subcutaneous tissue impedance measurement system.

In some embodiments the sensor array 101 includes a combination of any two of glucose, lactate and oxygen sensors. In other embodiments, the sensor array includes 101 includes at least one each of glucose, lactate, and oxygen sensors. In many embodiments, the respective sensors for glucose, lactate and oxygen are electrochemical sensors that include multiple electrodes or transducers that are dispersed along and/or among first sensor assembly 1001 and second sensor assembly 1002. For example, the glucose sensor can include a single or multiple glucose measuring electrodes found on either first or second sensor assemblies 1001 and 1002. Implementation of multiple electrodes for a particular analyte can enable redundancy or may be necessary to generate sufficient measurable electrical current.

The sensor array 101 further includes additional sensors or abilities to measure physical characteristics such as, but not limited to movement (via accelerometers), temperature, tissue impedance (such as tissue hydration levels related to development of edema), skin impedance and sensor hydration levels. The specific physical sensors discussed should not be construed as limiting. Other and additional physical characteristics from physical sensors associated with the sensor array 101 can be used as risk metric inputs to the risk score. Monitoring hydration levels of at least one some, or all of the sensors within the sensor array 101 enables detection of whether the sensor array 101 is properly implanted within desirable tissue. Additionally, monitoring the sensor elements for proper hydration can be used as a trigger to enable at least one of calculation of a risk score, data recording, and/or data transmission.

Electrochemical impedance spectroscopy applied across any electrode pair within the sensor array 101 can be used to measure or infer tissue impedance to determine tissue hydrations levels, or a fluid status within subcutaneous tissue of a subject being monitored. In some embodiments, fluid status of a subject is a risk metric contributing to the risk score of developing sepsis because fluid status provides context and a normalizing factor for other measurements, such as, and not limited to real time glucose, oxygen and lactate. Additionally, fluid status enables inference of capillary dysfunction which is an indicator of systemic inflammatory response syndrome (SIRS) or an ongoing progression of sepsis. Furthermore, absolute and trend information derived from tissue hydration levels enable adjustment or modifications to a risk score because goal directed fluid management can lose its effectiveness if the sign of fluid buildup (increasing tissue hydration levels or increasing rate of change of tissue hydration levels) are emerging. In still other embodiments, tissue hydration levels enable additional insight regarding perfusion of analytes within different types of tissues. For example, in various embodiments tissue hydration levels for a sensor array 101 placed in muscle provides additional or less information than a sensor array 101 that is placed in adipose tissue.

In some of these embodiments two of the three analyte sensor values are combined with data from any to all of the physical characteristic sensors to determine a risk score of developing sepsis. In other embodiments, all three of the analyte sensor values are used in conjunction with the data from any one to all of the physical characteristic sensors to determine a risk score of developing sepsis. The rationale for enabling risk score calculations based on less than all three analytes is to enable tailoring of the sensor array to a particular environment. For example, it may not be necessary to monitor glucose for a septic patient being monitored to determine efficacy of the therapy. Stated another way, for a patient already known to have sepsis, monitoring of glucose maybe optional because elevated glucose, as a metric within the system, is used to determine if an infection is progressing toward sepsis. Conversely, in an exemplary remote monitoring application where the objective is to identify early signs of the development of sepsis, the system may be highly tuned to monitor for elevations in glucose accompanied by decreases in tissue oxygen levels and optionally forgo any measurement of lactate.

In many embodiments, the analyte sensors are intended to be placed in subcutaneous tissue where the plurality of working electrodes within the sensor array 101 produce a corresponding plurality of signals. Placement within subcutaneous tissue enables a unique perspective for an oxygen sensor that is substantially different than common SpO2 oxygen measurements. Specifically, with embodiments of the analyte sensors 101a, oxygen within tissue is being measured rather than a measurement of SpO2 which is an estimation of arterial oxygen. When determining a risk score of developing sepsis it is advantageous to measure oxygen within tissue rather than estimated arterial oxygen because oxygen within tissue is a direct measurement of oxygen perfusion which is an early indicator of organ failure.

Supplementing the tissue oxygen signal are signals from the lactate and glucose sensors where each respective signal is proportional to an amount of analyte present in the subcutaneous tissue. In some embodiments, a two-electrode system is employed where each of the working electrodes electrochemically measure a particular analyte relative to a counter electrode. In other embodiments, a three-electrode system is employed where each of the working electrodes electrochemically measure a particular analyte relative to a counter and reference electrode.

In some embodiments, each working electrode has a corresponding counter electrode while in other embodiments multiple working electrodes share a counter electrode. In still other embodiments, two working electrodes share a counter electrode while the third working electrode has a dedicated discrete counter electrode. Furthermore, the various embodiments of working electrodes and counter electrodes can be distributed among separate and discrete substrates. Typically, working electrodes and counter/reference electrodes are formed on a single substrate. However, an electrode design intended for use in the invention allows the complete physical separation of any of the working electrodes and any of the counter/reference electrodes. For example, as is shown in FIGS. 1B-1 and 1B-2 working electrodes for analyte sensors can be formed on first sensor assembly 1001 while counter electrode are formed on second sensor assembly 1002. While the various electrodes may be separated on distinct substrates, in many embodiments the sensor array 101 having the plurality of working electrodes is inserted into the subcutaneous tissue via a single point of insertion. The use of a single insertion point minimizes both patient discomfort associated with insertion and insertion complexity.

The embodiments described above should not be construed as limiting. The sensor array should not be perceived as limited to subcutaneous placement for measurement of glucose, tissue oxygen and lactate. Other embodiments, for use in diagnosing or determining risk score for other conditions or diseases can employ various sensors to measure other combinations of analytes in different locations within the subject.

Electronics Module

Returning to FIG. 1A, the system 100 additionally includes an electronics module 102 that provides power for the sensor array 101 and enables bidirectional communication with other system components such as, but not limited to the external monitor 104, cloud computing systems 106 or mobile devices 128. Enabling the electronics module 102 to perform such tasks are electronic module components such as, but not limited to a communication module 108, a processor 110, memory 112, and a power supply 114 enclosed within an electronics module case. The electronics module 102 includes additional components, however, the specific components found in FIG. 1A warrant discussion regarding operation of the system 100.

In preferred embodiments the power supply 114 provides power to the electronics module 102 and also to the sensor array 101. Batteries, rechargeable or disposable, can be used for the power supply 114. In order to minimize the likelihood of fluid ingress to the electronics module, it may be preferable to use inductive charging for embodiments using rechargeable batteries. Other embodiments use alternatives to batteries such as, but not limited to capacitors, supercapacitors, solar cells, fuel cells and the like. The specific examples provided for the power supply 114 should not be construed as limiting. Rather, the examples provided should be viewed as examples of portable power supplies capable of supplying the electronics module 102 and the sensor array 101 with power for the expected life of the system 100.

In some embodiments the processor 110 is custom circuit such as but not limited to an application-specific integrated circuit (ASIC) or field programmable gate array (FPGA). In other embodiments the processor 110 is a more generic system on chip (SoC) or system in package (SiP). In instances where a SoC or SiP is utilized, communication module 108 and memory 112 can be integrated within the SoC or SiP. In many embodiments the processor is in communication with the sensor array 101 receiving raw signal data from the plurality of working electrodes and other sensors. In some embodiments the processor 110 performs minimal manipulation of the raw data from the working electrodes. Examples of minimal manipulation include, but are not limited to filtering noise and compression. In these embodiments the data from the working electrodes is transmitted to a multitude of external devices via the communication module 108 where processing is completed to produce a risk score for sepsis. Alternatively, in other embodiments the processor 110 executes stored instructions to process the sensor data before transmitting processed data that may include a risk score for sepsis to any external devices via the communications module 108.

Communications and Interconnectivity

In many embodiments the communications module 108 is based on personal area network technology commonly referred to as Bluetooth low energy (BLE) or Bluetooth Smart. In other embodiments, a customized or semi-custom communication standard is utilized. However, one common trait for any communication module 108 is the ability to securely send and receive data between at least a third party device and the electronics communication module 102. The ability to securely transmit either raw or processed data using the communications module 102 enables flexibility that allows the system 100 to be adaptable from a mobile monitor to being an integral component within a hospital ward.

In one embodiment data from the sensor array 101 is sent via the communications module 108 to a cloud computing system 106, also commonly referred to as "the cloud". In still other embodiments data from the sensor array 101 is transmitted via the communications module 108 to an external monitor 104. Clinical settings such as a hospital ward where multiple monitors display a plurality of condition being monitored for a patient could be ideal settings for embodiments where the electronics module 102 transmits to an external monitor 104 or the cloud 106. For example, with the appropriate infrastructure data from the sensor array 101 can be transmitted in real-time to an electronic medical record stored in the cloud 106. Alternatively, in some embodiments data can be transmitted from the external monitor 104 to the cloud 106 where it is stored as part of an electronic medical record.

In still other embodiments, the electronics module 102 transmits data from the sensor array 101 to a mobile device 128 such as, but not limited to a smartphone, a smartwatch, a portable fitness monitor, a tablet, a notebook computer, an ultrabook computer, or an aftermarket or integrated infotainment center for a vehicle. The examples of a mobile device 128 are not intended to be construed as limiting. Rather, the examples are intended to provide guidance regarding the types of devices that can receive and/or transmit data to the electronics module 102. Accordingly, devices that can be viewed as similar to those listed should be considered contemplated by the current disclosure. In embodiments where the mobile device 128 includes a connection to the internet, the mobile device 128 can send data to the cloud 106 where the data can be archived, shared with other devices, be further processed or become data to enable machine learning. Utilizing the data to enable machine learning further enables data-driven improvements such as development of algorithms that are patient specific or algorithms that are applied universally across all patients. For example, depending on how much information is provided with the data provided for machine learning, patient specific algorithms can include, but are not limited to factors such as age, race, weight, and pre-existing conditions. Similarly, regardless of patient specific information, all data processed via machine learning can be utilized to improve algorithms with the goal being improved outcomes for all patients.

Even with embodiments where additional processing is handled on either an external monitor 104 or the cloud 106, memory 112 can be used to store data from the sensor array 101 on the electronics module 102. Using the memory 112 to store data from the sensor array 101 can ensure sensor data is not lost if there are connectivity interruptions between the electronics module 102 and the external monitor 104, the cloud 106, or a mobile device 128. The memory 112 can further be used to store program instructions for the processor, or to store values for variables used by the processor 110 to output a risk factor for sepsis.

In many embodiments the electronics module 102 is removably coupled with the sensor array 101. With these embodiments, the electronics module 102 is capable of being reused after the sensor array 101 is deemed consumed or depleted. In other embodiments, a permanent coupling is achieved after an initial coupling between the electronic module 102 and the sensor array 101. In these embodiments, the electronics module 102 is considered disposable and is intended to be discarded after the sensor array 101 is deemed consumed. Alternatively, to reduce environmental impact, select portions of the electronics module, such as, but not limited to the power supply 114 and communications module 108 are recyclable. In many embodiments, initially coupling the electronics module 102 to the sensor array 101 provides power to the electrodes and initiates the program instructions stored in either the processor 110 or the memory 112.

In many of these embodiments, the electronics module includes a feedback device 113. The feedback device 113 provides feedback regarding the status of the combined electronics module 102 and sensor array 101. For example, in some embodiments the feedback device 113 is a single or a plurality of multi colored LED that blinks a first color and/or first pattern when the system is functioning with design parameters and a second color and/or second pattern if there is an error within the system. In other embodiments, the LED is a single color that uses different frequency of blinks to convey status of the system. In still other embodiments, the feedback module includes a vibration device similar those used in mobile phones to convey status of the system. In still other embodiments, a piezo or other audible sound emitting device is used as the feedback device 113.

The external monitor 104 may include some components not found in the electronics module 102, such as a graphic user interface (GUI) 122 and a display 124. Other components of the external monitor 104, such as a communication module 116, a processor 118, a memory and a power supply 126 may seem duplicative of components in the electronics module 102, but may have different or improved capabilities or functionality. For example, while the power supply 114 of the electronics module 102 may be a battery, the power supply 126 for the external monitor 104 may include an AC power supply that is supplemented with a rechargeable battery to enable the external monitor 104 to operate seamlessly between being plugged into a wall socket and being moved throughout a hospital until it can be eventually be plugged back into a wall socket.

For purposes of this invention, the GUI 122 further includes human interface devices that enable interaction with the GUI 122 such as but not limited to virtual or physical keyboards, touchscreens, joysticks, control pads and the like. Accordingly, use of the GUI 122 in conjunction with the display 124 enables user input to the system 100 and further allows selection or customization of what is shown on the display 124. The GUI 122 in conjunction with the communication module 116 and the communication module 108 further enables settings on the electronics module 102 to be manipulated or adjusted to optimize output from the system 100. Similarly, the GUI 122 enables user input to the processor 118 or the memory 120 to enable input and adjust settings that are applied to data from the sensor array 101 to determine a risk factor for sepsis.

The system further optionally includes a mobile device 128 having a user interface, such as, but not limited to a smartphone, a mobile phone, a smartwatch, a laptop, an ultrabook, a tablet computing device, a pager, and the like. The mobile device 128 is configured to receive data from the electronics module 102 via at least one of the cloud 106, the external monitor 104, or the electronics module 102 itself. In many embodiments the mobile device 128 is in bidirectional communication with the electronics module 102 which enables input via the user interface of the mobile device 128 to be transmitted to the electronic module 102. This enables a user of the mobile device 128 to manipulate, configure, or program settings on the electronics module 102. In some embodiments, bidirectional communications enables processing of data from the sensor array 101 on the mobile device 128. Additionally, in embodiments where the mobile device 128 includes a display, real time data and trends derived from the data is shown on the mobile device 128. In embodiments where the mobile device 128 includes at least one of an audible, tactile and visual alarm, the mobile device 128 can be used to update users of the mobile device 128 of the status of a patient wearing the sensor array 101. The status of the user includes, but is not limited to whether the system 100 is functioning properly, faults within the system 100, or real time measurements from the sensor array 101.

Another optional component within the system 100 is the cloud 106. Generally, the cloud 106 is considered some type of cloud computing which can be generalized as internet based computing that provides on demand shared computing processing resources and data to computer and other internet connected devices. In some embodiments the cloud 106 receives data from the electronics module 102 directly. In other embodiments data from the electronics module is transmitted to the mobile device 128 before being transmitted to the cloud 106. In still other embodiments, the cloud 106 receives data from the electronics module 102 via the external monitor 104. In still other embodiments, various permutations of communications initiated by the electronics module and transmitted between the external monitor 104 and the mobile device 128 results in data being transmitted to the cloud 106.

Data received by the cloud 106 may have already been processed by an intermediary device or can be processed on the cloud 106 and transmitted back to the intermediary device. In some embodiments, the cloud 106 contains electronic medical records and data from the sensor array 101 is automatically uploaded to the electronic medical records. With real time data being uploaded to the cloud, it becomes possible to apply machine learning which can further enable automatic or semi-automatic adjustments to the electronics module 102. Automatic updating would result in changes to the programming of the electronics module without human intervention whereas semi-automatic updating would require someone to confirm changes to the programming of the electronics module 102. In one example, the cloud 106 enables examination of medical history such as pre-existing conditions and family history and machine learning can suggest or set customized thresholds and sensor sampling rates based on previous data from patients with similar conditions and data The previously discussed components or elements within the system 100 are intended to be exemplary rather than limiting. As the system is intended to be flexible components are able to be added and removed based on immediate needs. This includes enabling or disabling system components within one environment while enabling or disabling the same system components at a later point. For example, a facility utilizing the system for triage may not implement or enable communications to mobile device 128 while enabling communication with the cloud 106. However, once a patient is moved from triage to a monitoring or remote monitoring environment, communication with a mobile device may be enabled. Similarly, a hospice may choose to not enable communication with the cloud 106.

Determining the Risk Score—Processing Sensor Data

Figure 2A:
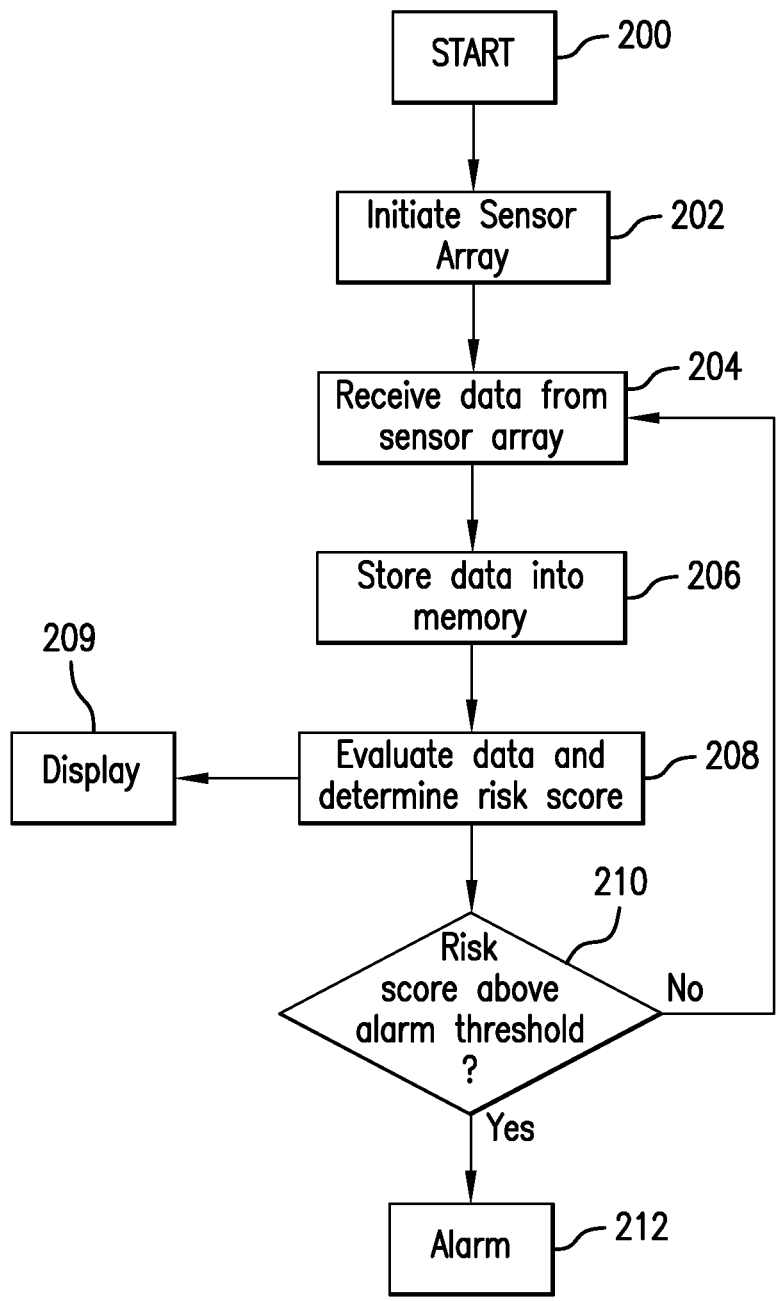
FIG. 2A is an exemplary flowchart illustrating operations performed by various components of the system to determine a risk score for sepsis, in accordance with embodiments of the invention.

FIG. 2A is an exemplary flowchart illustrating operations performed by various components of the system 100 to determine a risk score for sepsis, in accordance with embodiments of the invention. The flowchart begins with start operation 200 followed by operation 202 that initiates the sensor array. In many embodiments, operation 202 occurs when electrical contact is made between the power supply in the electronics module and the working electrodes within the sensor array. In operation 204, data is received from the sensor array. In some embodiments data is received at the processor associated with the electronics module. Alternatively, in other embodiments the data can be viewed as being received from the electronics module at an external monitor, a mobile device or the cloud.

Operation 206 takes the received data and stores it in a memory. The memory can be associated with the electronics module, an external monitor, the cloud or the mobile device. With operation 208 data from the sensor array is evaluated using the processor. Similar to storing the data, evaluation of the data can occur on the electronics module or any number of devices in communication with the electronics module such as the external monitor, the cloud or a mobile device. The risk score determined by operation 208 is output to operation 209 that displays the risk score. The risk score from operation 208 is also passed to operation 210 that determines if the risk score exceeds an alarm threshold value. If a risk score threshold value is exceeded, operation 212 outputs an alarm such as an audible, visual, tactile or combination thereof. Embodiments having the requisite infrastructure can enable alarms or alerting at remote locations such as, but not limited to external monitors, mobile devices and other cloud connected devices. If the risk score is below an alarm threshold, the flowchart returns to operation 204 where new data from the sensor array is received.

Figure 2B:
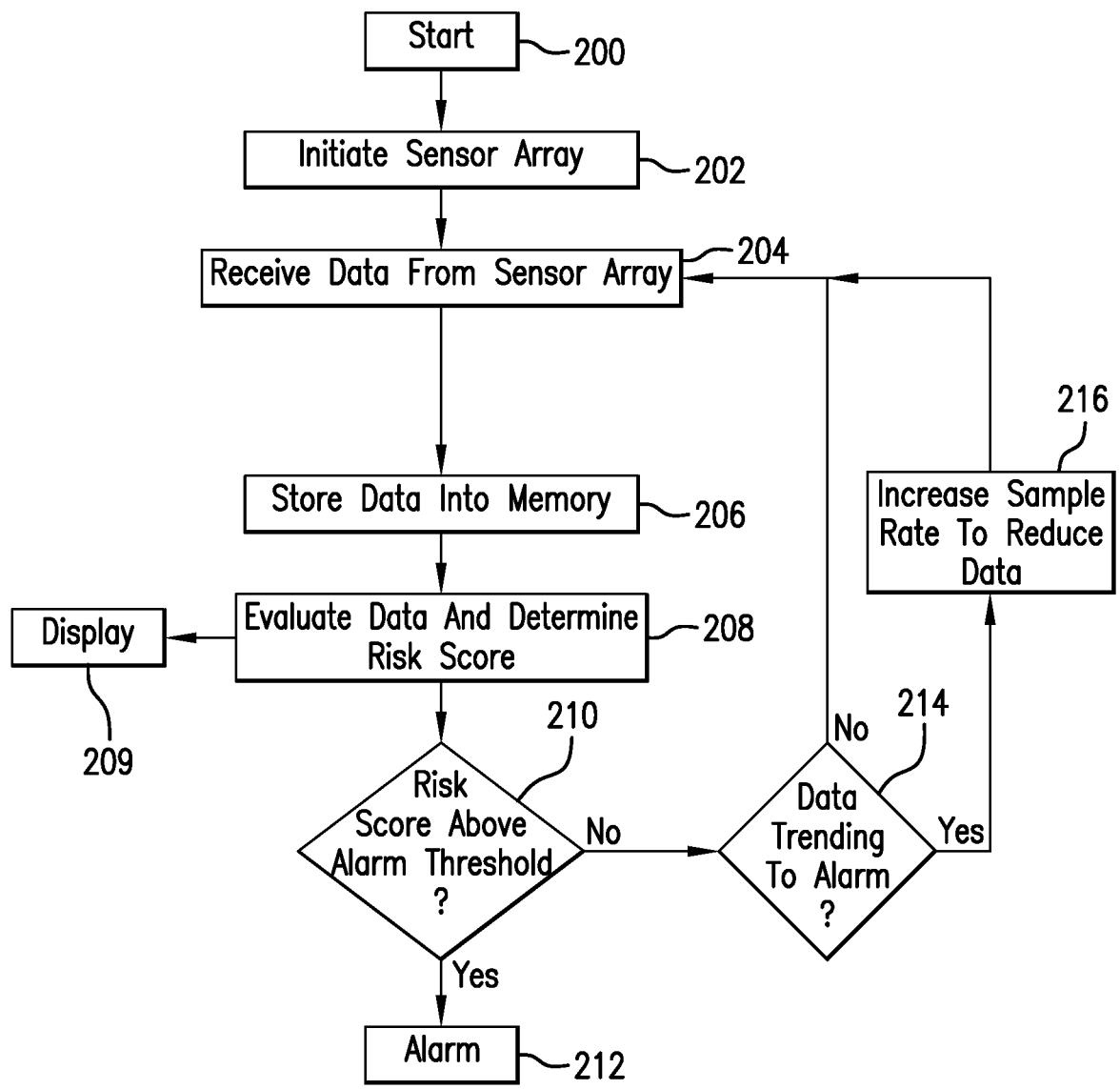
FIG. 2B is an alternative embodiment of FIG. 2A, in accordance with embodiments of the invention.

FIG. 2B is an alternative embodiment of FIG. 2A that executes operation 214 after operation 210. Operation 214 determines if the evaluated data is trending toward an alarm threshold. If the data is trending toward an alarm condition, operation 216 increases the data sampling rate so data is received at operation 204 at a higher rate. If the data is not trending toward an alarm condition the flowchart returns to operation 204 where additional data is received from the sensor array. One advantage of increasing the sampling rate is to achieve improved resolution of the rate of change of an analyte. Selectively changing the sampling rate based on real time conditions, or dynamic sampling, can be implemented in various ways because the risk score is determined from multiple analytes. In one embodiment each working electrode has a dynamic sample rate that is completely independent from the sampling rate of the other working electrodes. In another embodiment, the sample rate of all of the working electrodes is dynamically tied the output of a single working electrode. However, with embodiments that increase the sample rate of all the electrodes, it may not be necessary to utilize all of the data when determining a risk score. Accordingly, in some embodiments, even with increased sampling rates, particular metrics may be determined on data gathered at rates other than the sample rate. For example, if a rate of change of oxygen results in increased sampling rates for all analytes, the calculations for the rate of change of lactate may not be based on the increased sampling rate. However, if lactate levels or the rate of change of lactate eventually indicate that increased sampling rates would be beneficial, the rate of change of lactate calculations can be based on the increased sampling rate. Alternatively, the overall sampling rate of all the electrodes can be further increased beyond the original increase for oxygen. Thus, the rate of change for lactate can push for higher sampling rates and the oxygen calculations can continue to be made at the original increased frequency. Thus, while an overall sampling rate may be implemented across all of the working electrodes, the calculations for the respective analytes may be dynamically determined on a preferred sample rate for each analyte.

Figures 1, 3A:
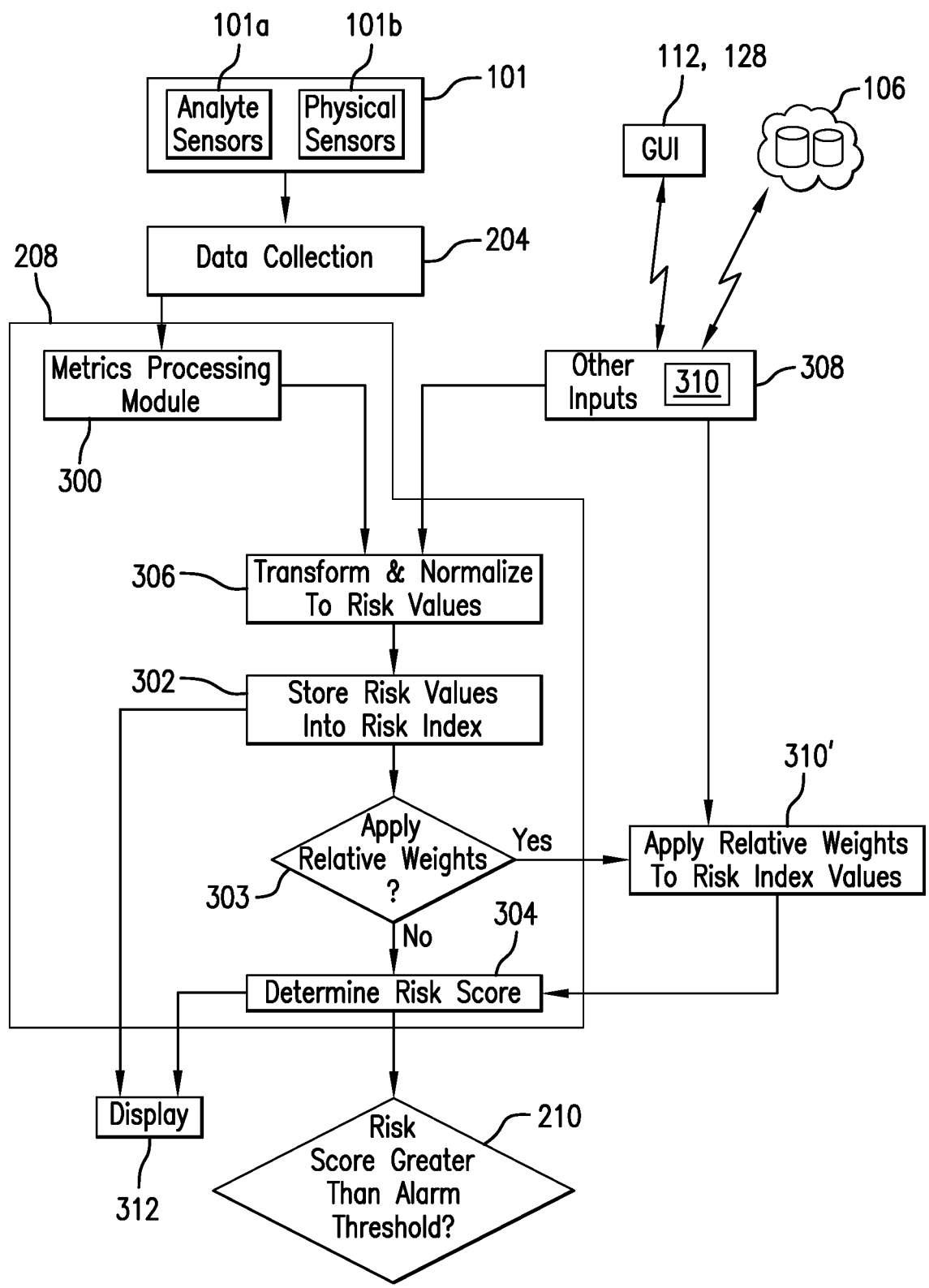
Figures 2, 3A:
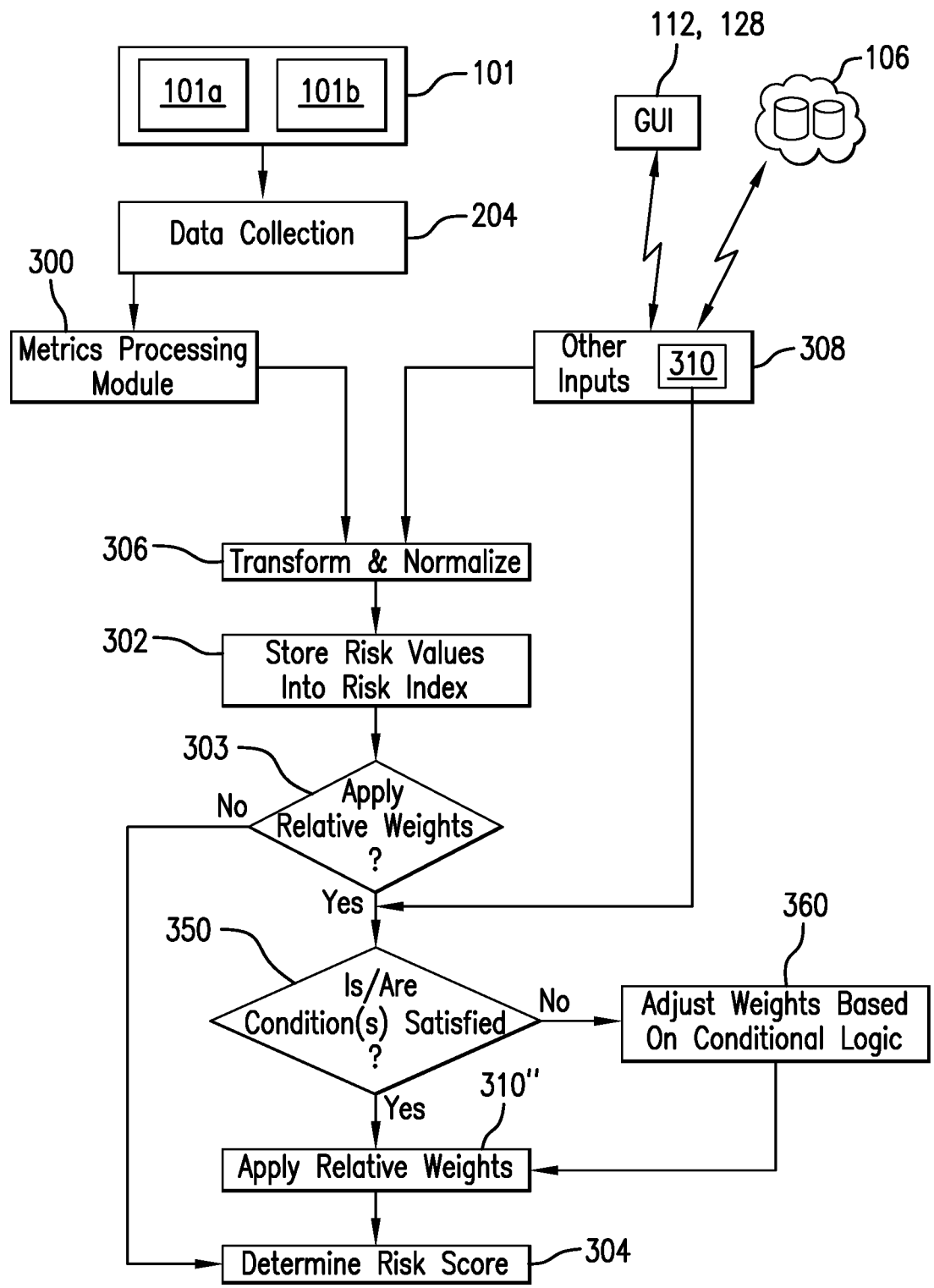

FIG. 3A-1 is an exemplary hybrid flowchart and block diagram illustrating operations and elements used to perform operation 208 that evaluates risk metrics provided by the sensor array 101 and other inputs 308 to determine a risk score, in accordance with embodiments of the invention. The sensor array 101 includes analyte sensors 101*a* and physical sensors 101*b*. In many embodiments physical sensors 101*b* include, but are not limited to sensors like accelerometers and thermometers that respectively generate risk metrics such as movement and temperature. The analyte sensors 101*a* include, but are not limited to sensors that measure risk metrics like glucose, oxygen, and lactate in real-time within subcutaneous tissue.

In preferred embodiments, a single point of entry is used to insert the analyte sensors 101a within subcutaneous tissue. Depending on the types of physical sensors included within the sensor array 101, some physical sensors may be implanted within subcutaneous tissue while other physical sensors remain outside of the subject but still incorporated within the electronics module. In these embodiments, the analyte sensors are implanted with via a single point of entry but some or all of the physical sensors are coupled with the sensor assembly concomitant with attachment of the electronics module. Despite using a single point of entry, in some embodiments the analyte sensors 101a are distributed among multiple separate substrates. However, in other embodiments, the analyte sensors 101a are disposed, or located, on a single substrate. Irrespective of relative placement of the analyte sensors 101a, operation 204 collects data from the analyte sensors 101a and the physical sensors 101b and in accordance with operation 206 of FIGS. 2A and 2B, stores the data into a memory. The physical location the memory 206 may vary between being located within the electronics module 102, on the external monitor 103 the cloud 106 or the mobile device 116. Regardless of where the data from the sensor array 101 is stored, operation 208 evaluates the data to determine a risk score of developing sepsis.

As shown in FIG. 3A-1, operation 208 is dependent on data collected from the sensor array 101. Operation 208 can be supplemented with other inputs 308 to improve or enhance determination of a risk score, but other inputs 308 are not required to determine a risk score. It is the real-time measurements of glucose, lactate, and tissue oxygen risk metrics that enable determination of a risk score for developing sepsis across multiple environments. For purposes of this disclosure "real-time" or "substantially real-time" should be construed to mean the actual time during which something takes place, or within milliseconds so the measurement is available virtually immediately.

Within operation 208 a metrics processing module 300 receives sensor data that was previously stored in memory by operation 206. Exemplary inputs to the metrics processing module 300 include primary inputs, or primary data, that are defined as signal data received from the sensors array for measured risk metrics such as glucose, lactate, tissue oxygen, tissue hydration, temperature and the like. In many embodiments the metrics processing module 300 allows the primary inputs to be passed through to operation 306. In other embodiments, the metrics processing module 300 also calculates secondary inputs which are defined as inputs or metrics that are calculated based on primary inputs before being input to operation 306.

Examples of secondary inputs include, but are not limited to ratios between primary inputs, rates of change of primary inputs, and rates of changes of ratios between primary inputs. Inclusion of secondary inputs can improve or enhance the determination of the risk score because specific changes in specific ratios of measured analytes, or primary inputs, can be an indicator of dysregulation, or the development of sepsis. An example of a secondary input that can be valuable in determining a risk score for sepsis is the ratio of glucose to tissue oxygen. This ratio can contribute to the risk score because an increase in glucose relative to tissue oxygen can be indicative of hypoxia, a precursor to sepsis. Another secondary input, the ratio of lactate to tissue oxygen, is indicative of hypoxia, when there is an increase in lactate relative to tissue oxygen. Still another secondary input that is an exemplary precursor to sepsis is the ratio of glucose to lactate. A measurable increase in glucose concentration relative to lactate can be suggestive of anaerobic glycolysis, another precursor to sepsis. Accordingly, operation 300 can be summarized as receiving primary inputs (analyte sensor data and physical sensor data) and outputting to operation 306 both primary inputs and secondary inputs (metrics calculated based on primary inputs).

Optionally supplementing operation 306 are other inputs 308 that are based or derived from external data obtained from outside the sensor array, and this can include additional risk metrics along with a subset of relative weights 310. Relative weights 310 are used to modify primary, secondary and other inputs and will be discussed in more detail regarding operation 310'. Other inputs 308 are defined as risk metrics that impact a risk score that are not measured by the sensor array 101, and may even be used to determine a risk score without any input at all from the sensor array. For clarity, other inputs 308 may include discrete measurements of a risk metric (e.g. a one-off lab test), periodic/episodic risk metrics (e.g. periodic test results, periodic discrete analyte(s) measurement(s) with finger pricks, etc.) or continuous real-time measurements from supplemental medical monitors (such as heart rate, blood pressure, or even peripheral oxygen saturation rates using non-invasive pulse oximetry as an approximation of the more accurate invasive measurement of tissue oxygen via the sensor array 101). Examples of other inputs 308 include, but are not limited to data or metrics commonly available from lab/clinical tests, or continuously collected through readily available hospital monitoring equipment. If enabled, some embodiments receive other inputs 308 from electronic medical records stored in cloud 106. Alternatively, a GUI associated with a monitor or mobile device can be used to supply other inputs 308. For example, other inputs 308 include risk metrics such as, but not limited to heart rate, respiratory rate, urine volume, blood pressure, cognitive/neurological assessment scores, and age. For other inputs 308 that are based on measured values like the sample above, some embodiments of other inputs 308 enable calculations of rates of change and ratios between various other inputs. For example, rates of change of heart rate and rates of change of blood pressure. Other inputs 308 can further include any disease states of a subject along with any associated comorbidity risk factors. Inclusion of disease states or particular chronic illnesses further enhances the ability to determine a meaningful risk score of developing sepsis, and the following chronic disease states listed in decreasing order of risk, can contribute to an increased risk of developing sepsis: AIDS, liver failure, cancer, and generally immune compromised patients.

Operation 306 receives risk metrics in the form of primary and secondary inputs from the metrics processing module 300 along with any other inputs 308 and transforms and normalizes the various inputs into risk values that are functions of the original risk metrics. In preferred embodiments, the risk values are a number between zero and one where one is a high risk for developing sepsis and zero is a low risk for developing sepsis. When transforming and normalizing primary and secondary inputs, one embodiment looks for deviations from baselines to determine a risk value. In another embodiment, the risk value is determined by comparing measured primary and secondary inputs to threshold values. The transformation and normalization performed by operation 306 converts individual risk metrics to unitless risk values that enables comparison and relative weighting to be applied across the risk values.

The output of operation 306, the risk values between zero and one, are input into operation 302 that stores the risk values into a risk index. The risk index is defined as a compendium of all of the transformed and normalized risk values. Storage of the risk values within the risk index enables any or all of the individual risk values to be displayed in operation 312. Display of individual risk values can help provide context to a health care provider regarding particular risk metrics within the risk score. For example, inclusion of the risk index enables operation 312 to display lactate trends for a subject which can further provide context and insight into the behavior of the risk score. Without storage of the risk values within the risk index, a healthcare provider may only be able to see the end result risk score without context of the risk values. This could lead a healthcare provider to speculate the cause of the risk score behavior rather than simply being able to see changes in the risk values over time on a display.

A next operation 303 determines if relative weights are applied to the risk values within the risk index. If relative weights are not applied, operation 304 determines the risk score by taking the sum of the risk values. If relative weights are applied, operation 310' applies relative weights 310 to appropriate risk values before operation 304 then calculates a weighted average risk score.

The following are examples of reasons it may be preferred to use other inputs 308 (such as information on a chronic illness or disease state) as relative weights 310 that modify the calculation of a risk score. When a subject being monitored is diabetic there may be greater variations in glucose measurements. Diabetes can further affect lactate measurements as both ketoacidosis and metformin consumption may lead to increased lactate in a subject already predisposed to generally higher lactate levels. Other examples of chronic conditions that can affect lactate levels include, but are not limited to metastatic cancer, leukemia/lymphoma, or the presence of solid tumors. Accordingly, associating a relative weight to specific risk metrics affected by particular pre-existing or chronic condition such as diabetes, cancer, leukemia or other immune-compromised condition enables emphasis or de-emphasis of single, multiple, or all primary, secondary and other inputs.

Figure 5:
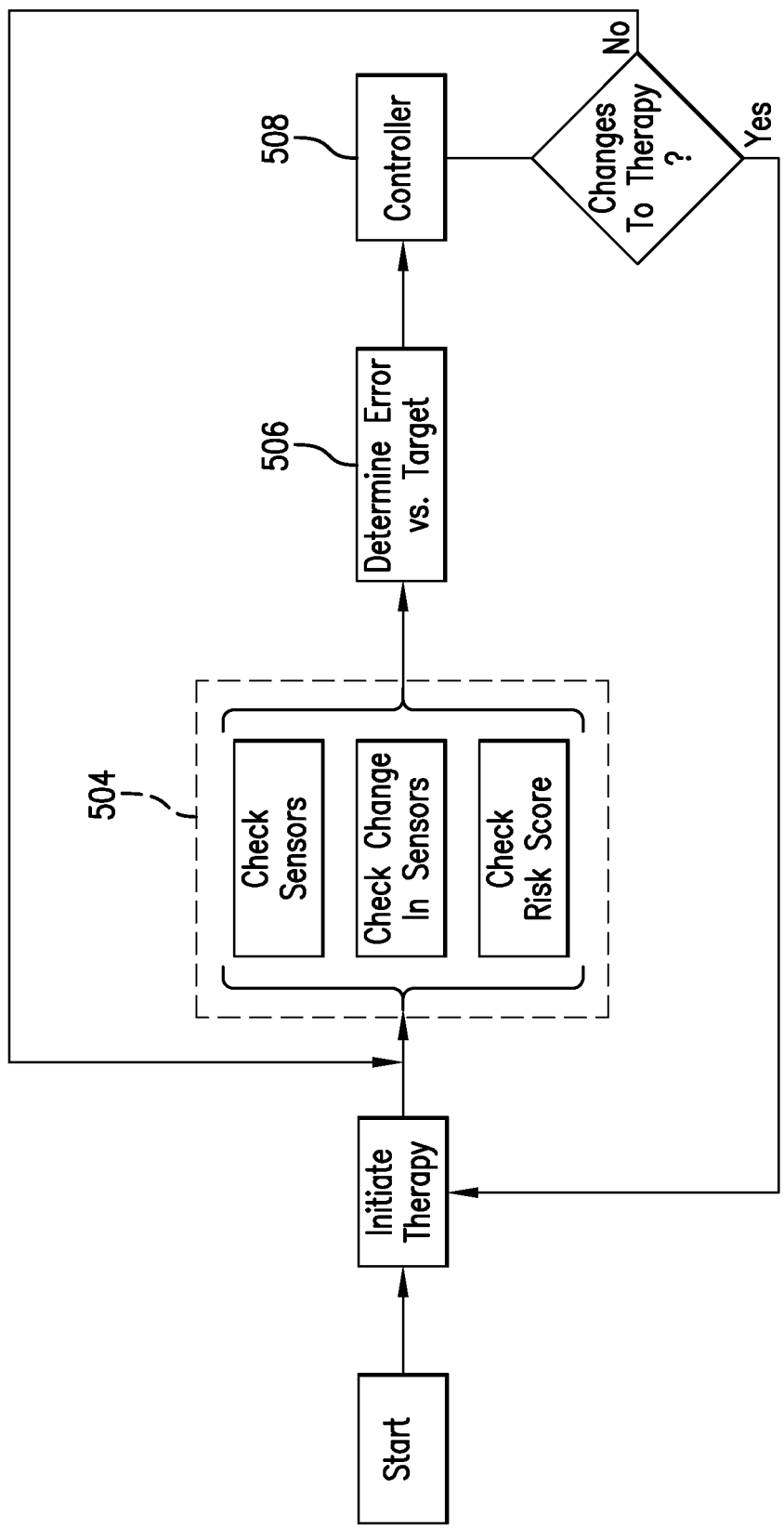
FIG. 5 is an exemplary flowchart illustrating integration of the system within a therapy management system to enable a feedback mode in accordance with embodiments of the invention.

FIG. 5 is a table of exemplary relative weights that can be applied to various risk metrics when a system is applied in a triage environment for a non-diabetic subject and a diabetic subject. As shown in FIG. 5, the relative weights of zero ensures that the greater variations in glucose measurements from a diabetic subject do not influence determination of the risk score in triage mode. However, the autoimmune disorder relative weight of three may result in an overall more conservative determination of a risk score. FIG. 5 is intended to be an exemplary illustration of how relative weights can be used to influence different primary and secondary metrics used to determine the risk score of developing sepsis. Other chronic disease states may require different relative weights based on how the disease state impacts a particular metric.

Other relative weights 310 can also be customized or tailored to be specific to a particular hospital, health system, physician or patient need. For example, the relative weights 310 may be customized to better fit a particular hospital workflow such as where a hospital intensive care unit already utilizes sepsis scorecards that assign different relative weights to various lab/clinical tests. In these embodiments, the relative weights 310 for the system can be customized to follow similar, if not exact matches to the existing sepsis scorecards. Similarly, the relative weights can be adjusted based on the whether the patient is in a triage, patient monitoring or remote monitoring environment. FIG. 6 includes a table of exemplary relative weighting coefficients that can be applied to various risk metrics based on the subject's environment.

The examples discussed above are intended to be exemplary and should not be construed as limiting, especially regarding the analytes and combinations thereof. Other embodiments capable of measuring different, alternate or additional analytes or risk metrics to derive a risk score of developing sepsis or other disease or physical condition should be considered within the scope of this disclosure.

The output of operation 304, the risk score, is used as input into operation 210 that determines if the risk score is greater than an alarm threshold and the flowchart is completed as shown in FIGS. 2A and 2B. Note, operation 208 is capable of providing output to a display on a hospital monitor, mobile device, or other screen based on output from either operation 302 of the risk values within the risk index and/or the risk score from operation 304. Accordingly, operation 312 is intended to display visual representation of real-time and/or historical data such as the risk score or individual risk values from within the risk index. For example, in some embodiments, particularly those in the patient monitoring environment, real time charts of the measured analyte data are shown on a display 312 in addition to a final risk score. In other embodiments, such as those in the remote monitoring environment, a simplified display showing the resulting risk index is displayed on a mobile device such as a smartphone. In embodiments where data from the remote monitoring device is concurrently being reviewed by an attending physician, additional data such as real time charts from the chemical sensors may be displayed for the physician. The ability to display individual risk values can provide meaningful insight to physicians and medical staff regarding changes, or lack of changes to the risk score.

FIG. 3A-2 is an exemplary hybrid flowchart and block diagram further including the application of conditional logic or conditional weights, in accordance with embodiments of the invention. The ability to include conditional logic allows use of prior outputs as input thereby enabling more complex methods to determine a risk score. Differentiation between FIG. 3A-1 and FIG. 3A-2 manifest when operation 303 determines that relative weighting is applied to the risk values. In FIG. 3A-2, if the risk values are augmented by relative weighting, the relative weights 310 are carried into operation 350 that determines if a conditions, or conditions, have been satisfied. The condition, or conditions are drawn from anything measured by, or input into the system or stored in the system memory. For example, conditions may be applied to primary or secondary inputs, risk values or a previously determined risk score. Failure to meet a condition can results in adjustments being made to a single relative weight for the single risk value, adjustments to the relative weights for other risk values, or adjustment to the relative weights of all the risk values.

In an exemplary embodiment there are conditions for risk values associated with oxygen, impedance, rate of change of temperature. In this example the condition for oxygen is not met resulting in an adjustment being made to a relative weight. The relative weight being adjusted can be for oxygen, impedance, rate of change of temperature or any other primary, secondary input, risk value or even previously determined risk score. Additionally embodiments include conditions that are chained, like a conditional tree with branches for decisions points. For example, if oxygen and glucose risk values hit independent target thresholds, make an adjustment to the relative weighting factor for lactate. The particular conditions and changes to relative weights discussed above are intended to be exemplary rather than comprehensive. Other conditions, or combinations of conditions can drive changes to the relative weights to further improve the determination of the risk score.

If the condition, or conditions of operation 350, are not satisfied operation 360 adjusts the relative weights 310 before passing the adjusted relative weights to operation 310" that applies the adjusted relative weights to the risk values. If the condition or conditions of operation 350 are satisfied, operation 310" applies the unadjusted relative weights 310 to the risk values. In a later operation, 304, the risk score is determined based on risk values untouched by relative weights from operation 303, or risk values that have been adjusted with either adjusted relative weights or original relative weights.

Figure 3B:
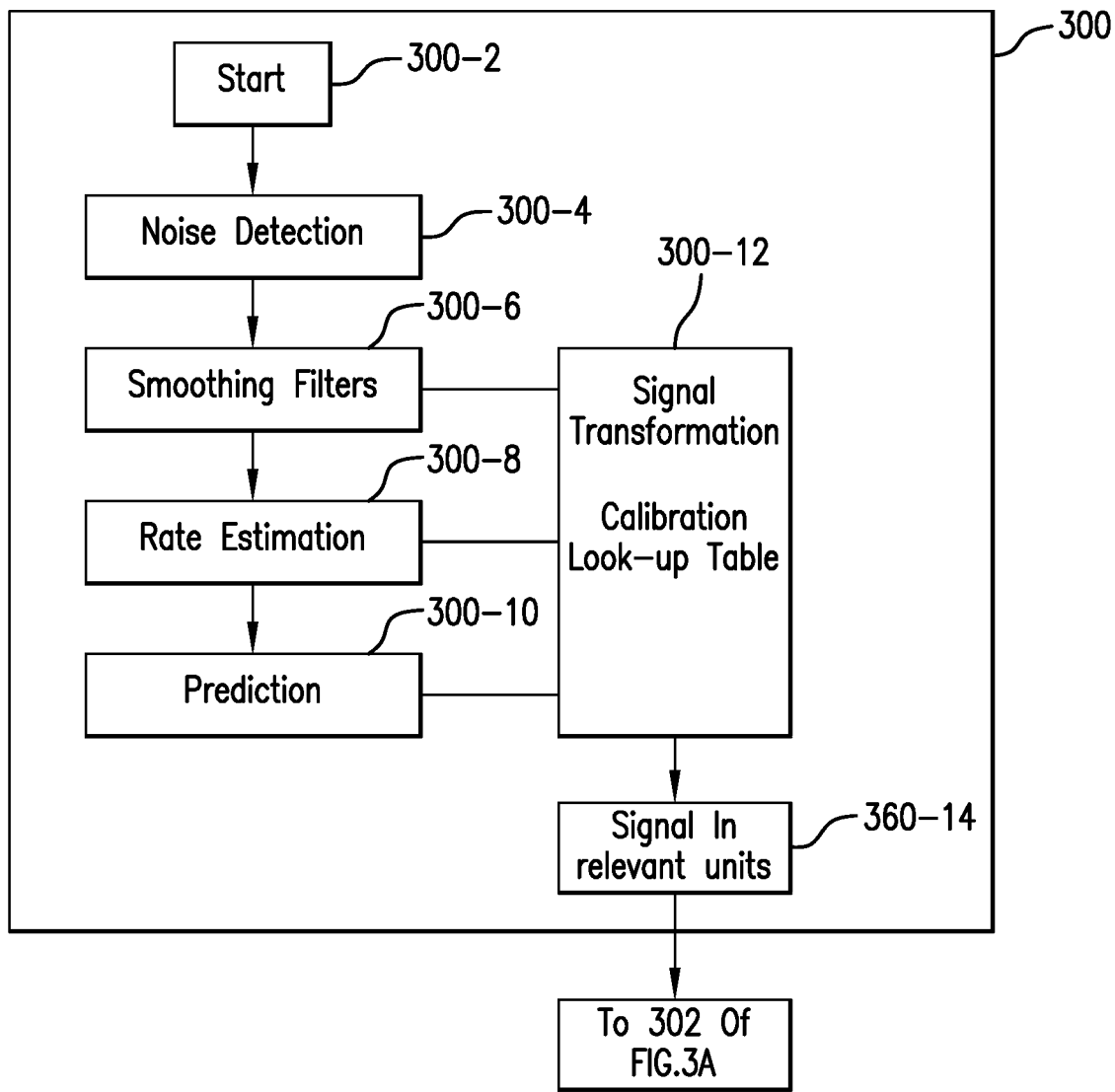
FIG. 3B is a hybrid flowchart and block diagram illustrating exemplary operations within the metrics processing module, in accordance with embodiments of the invention.

FIG. 3B is a hybrid flowchart and block diagram illustrating exemplary operations within the metrics processing module 300, in accordance with embodiments of the invention. Operation 300-2 starts processing primary data that enters the metrics processing module 300. Subsequent operation 300-4 applies noise detection and operation 300-6 applies smoothing filters, to the primary data within the metrics processing module 300. The output from operation 300-6 is passed to operation 300-8 that uses smoothed primary data to determine rate estimations or the first type of secondary input or secondary data. Subsequently, rate estimations from operation 300-8 are used by operation 300-10 to determine predictive values. The output of operations 300-6, 300-8 and 300-10 are also provided to operation 300-12 that performs a first signal transformation. In some embodiments the signal transformation includes, but is not limited to calibration or utilization of look-up tables to transform or translate the respective signals into relevant units. For example, when primary input such as glucose data enters operation 300 it may be in the form of measured current from the working electrode of the multianalyte sensor. After passing through operation 300-6 and upon completion of operation 300-12, the original current measurement is transformed or translated into an instantaneous concentration of glucose in units such as millimole of glucose. When utilized within the scope of a triage scenario, instantaneous measurements of primary inputs glucose, lactate, and tissue oxygen help determine if conditions within the subject are indicative of sepsis when the measurements deviate significantly from normal ranges.

The metrics processing module 300 is also capable of looking at measurements over windows of time, or the rates of change of primary inputs, and provide additional insight or even a predictive capability for detecting conditions that can lead to the onset of sepsis. For example, rates of change of data measured by the sensor array and passed through both operations 300-8 and 300-12 result in the rates of change of lactate, glucose and tissue oxygen. Additionally, predicted measurement of glucose, lactate and tissue oxygen are also output if data passes through operations 300-10 and 300-12.

An example of using predictive measurements to determine a risk score is found when examining stress-induced hyperglycemia, a known marker for sepsis. Accordingly, the ability to detect or predict the onset of high blood glucose levels is extremely desirable when developing the risk score of developing sepsis. To obtain the prediction a projection in time can be achieved by calculating a trend from recent glucose concentrations values, or in one embodiment, the change of glucose measurement over time, or more simply, the glucose derivative. A common method to estimate the glucose derivative is to apply convolution (i.e. Savitzky-Golay filtering algorithm) to the data. In other embodiments, future glucose measurement are estimated using more advanced algorithms that additionally use the noise content of the signal as an input to compute the prediction (i.e. a Kalman filter).

Regardless of the specific filter applied to the data to determine a predicted value, the predicted value may be included as a risk metric when determining the risk score for the onset of sepsis. However, due to relative uncertainty related to predictions and projections into the future, any predicted value can be adjusted appropriately via relative weight 310 that can be applied to adjust risk scores. Accordingly, for many embodiments, the relative weight for predicted glucose may be lower than the relative weight for instantaneous glucose measurements. However, in still other embodiments, the relative weights for the various data points and rates of change may be tuned to optimize for either certainty or predictive capability.

Another indicator or signal of the onset of sepsis is lack of glycemic control. With some embodiments of the invention a time-in-range calculation or a time-out-of-range metric, normalized to a percentage of the evaluated window time is used as a metric to reflect the ability of the patient to manage glucose concentrations. Glycemic control, unlike the previously discussed trend and predictive data, is a trailing indicator and requires significantly more time (i.e. data points) before a reasonable calculation can be made. For example, the glycemic control metric may require hours, or even multiple days' worth of data points instead of the minutes of data required for predictive metrics. Accordingly, effective use of a glycemic control metric may be found when the system is utilized in an outpatient setting to monitor trends over extended periods of time.

As with glucose concentrations, elevated lactate concentrations are a marker for sepsis and the onset of sepsis. Conversely, decreasing oxygen saturation is also associated with an increased risk of sepsis. Following the same methods described above for glucose, trending data for lactate concentrations may similarly be calculated to support acute prediction/diagnosis of sepsis. Likewise, calculation of oxygen saturation rate of change should follow the same algorithms used for glucose and lactate. However, unlike glucose, naturally decreasing lactate concentration, or clearance of lactate, by the body is a signal of decreasing risk of sepsis. Thus, a negative lactate rate of change would represent one of the few negative risk values. Similarly, elevated lactate concentrations coinciding with regular or faster than regular lactate clearance may not be considered cause for alarm because the subject continues to clear lactate from the body at a regular or above regular rate.

Figure 4A:
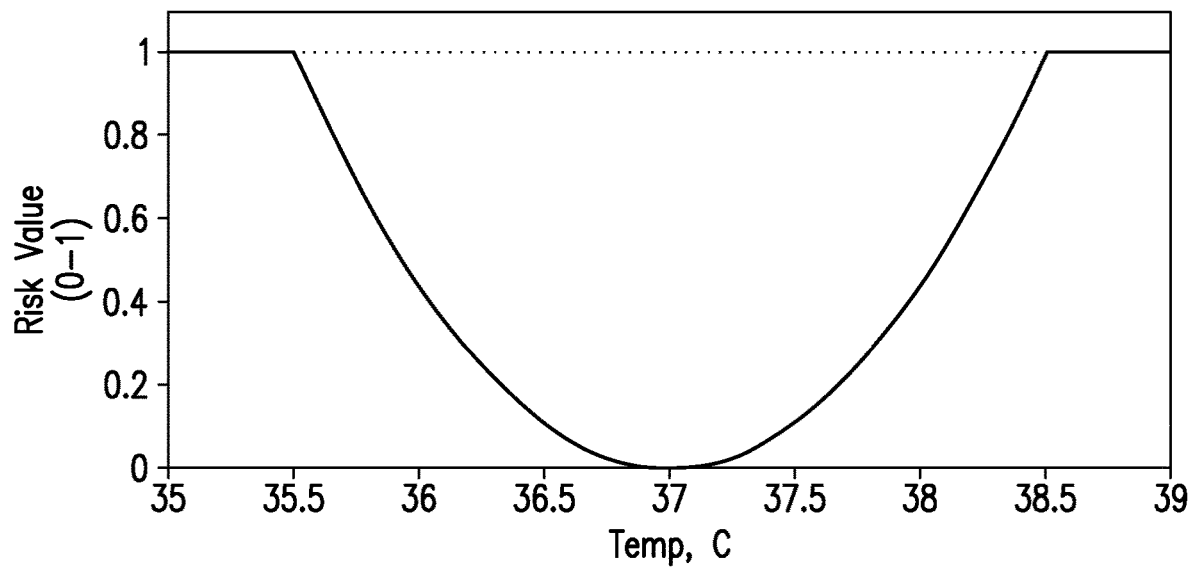
FIG. 4A is an exemplary chart illustrating how temperature risk metrics are converted to normalized temperature risk values, in accordance with embodiments of the invention.

FIG. 4A is an exemplary chart illustrating how temperature risk metrics are converted to normalized temperature risk values, in accordance with embodiments of the invention. With infections, immune response typically results in an initial increase in body temperature. As dysregulation occurs associated with organ failure, hypothermia becomes a possibility. However, in either situation, hypothermia or hyperthermia, deviation from normal body temperature is associated with increased risk of mortality. As shown in FIG. 4A, normothermia is centered around 37 Celsius and is associated with a very low risk value. However, as temperature deviates toward either hypothermia or hyperthermia, the temperature risk value begins to increase toward a value of one.

Figure 4B:
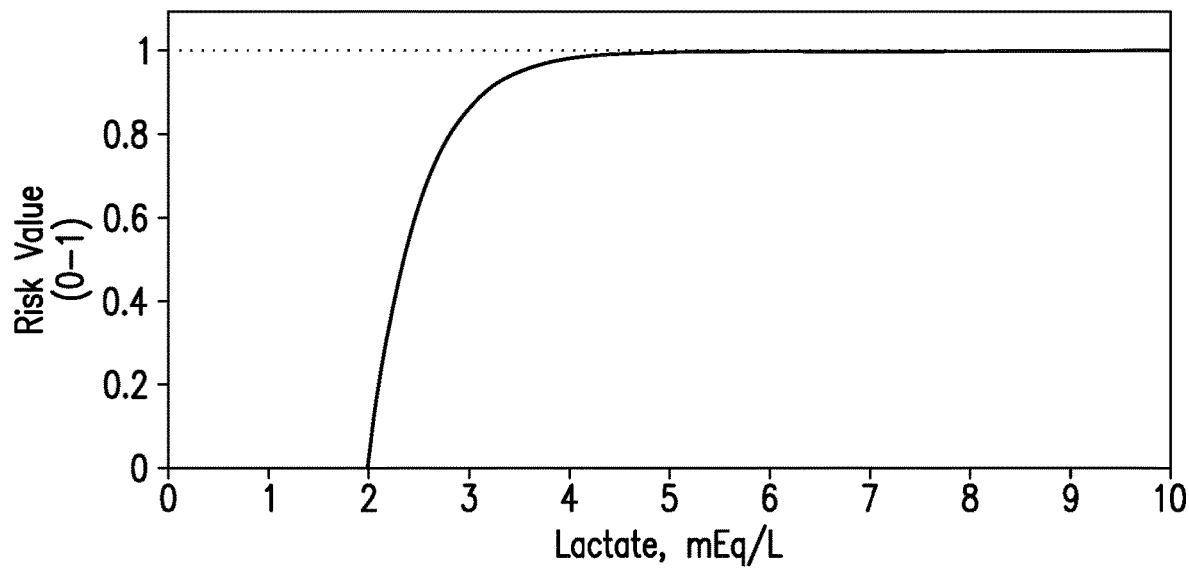
FIG. 4B is an exemplary chart illustrating conversion of lactate sensor readings to normalized lactate risk values, in accordance with embodiments of the invention.

FIG. 4B is an exemplary chart illustrating conversion of lactate sensor readings to normalized lactate risk values, in accordance with embodiments of the invention. Normal plasma lactate concentration is 0.5 to 1.5 milliequivalents per liter. Lactic acidosis is generally defined as a plasma lactate concentration greater than 4 milliequivalents per liter, even in the absence of overt academia. In sepsis, the inability of the body to support lactic acid clearance results in increased levels of lactate, as high as 20 milliequivalents per liter. In light of the previously disclosed risks associated with lactate concentrations, the lactate risk value increases sharply upon exceeding 2.0 milliequivalents per liter and reaching a maximum of 1 after the lactate concentration approaches limits outside of lactic acidosis. However, because acute increases (followed by gradual decreases) in lactate concentration can occur as a result of physical exertion such as exercise, for remote monitoring embodiments the maximum relative weighting factor can be limited to 0.5 rather than 1 for lactate concentrations between four and six milliequivalents per liter. In still further embodiments, the change of lactate risk value based on exercise occurs automatically when a physical sensor measuring movement detects continuous motion associated with exercise. Other modifications to the lactate risk value chart can be made based on other inputs such as, but not limited to chronic disease states and certain types of medication.

Figure 4C:
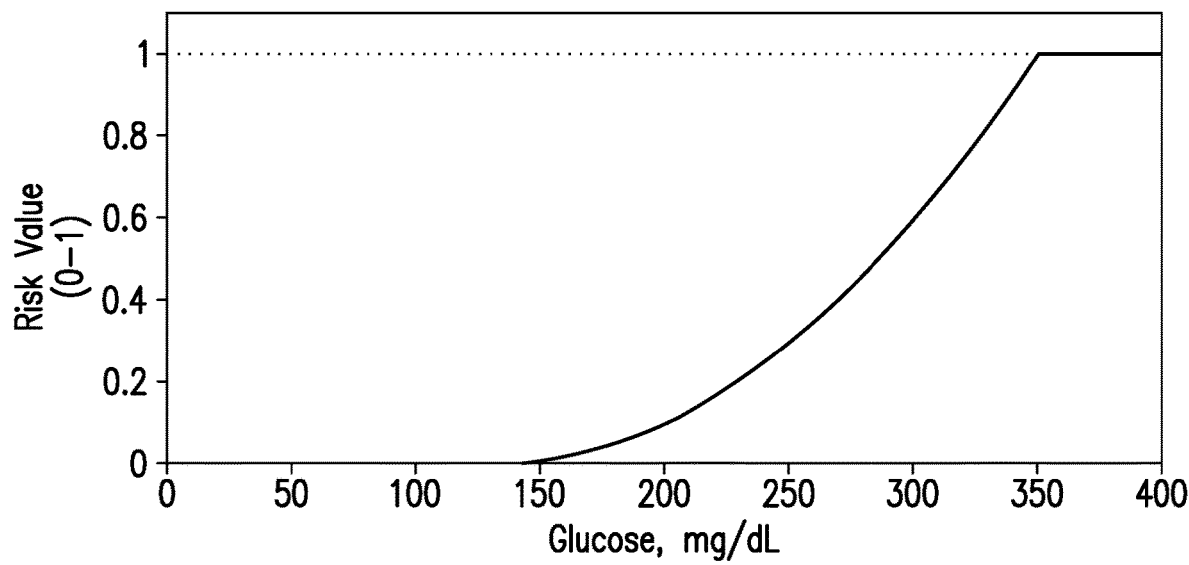
FIGS. 4C and 4D are exemplary charts illustrating how glucose risk values can change, in accordance with embodiments of the invention.
Figure 4D:
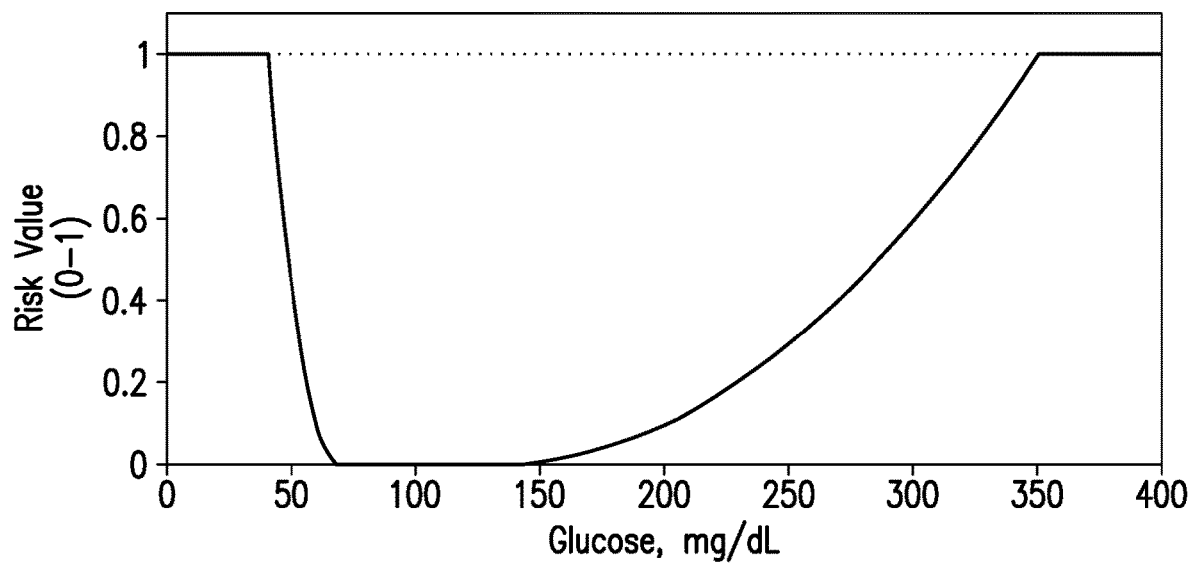

FIGS. 4C and 4D are exemplary charts illustrating how glucose risk values can change in accordance with embodiments of the invention. The American Diabetes Association defines tight glucose control is achieved between the range of 3.9-7.2 millimol/L (70-130 mg/dL). Deviations outside of this range are correlated with long-term health effects typically associated with diabetes mellitus. Similarly, in the intensive care unit setting both hypoglycemia and hyperglycemia are associated with increased mortality with hypoglycemia carrying a greater risk of death. In the case of sepsis, an argument can be made to exclusively track hyperglycemia because sepsis is correlated with elevated glucose levels. FIG. 4C is an exemplary chart of glucose risk values that places a greater risk of developing sepsis on hyperglycemia.

In embodiments that take into consideration mortality rates rather than strictly sepsis detection and diagnosis, the risk index can further include consideration of hypoglycemia. Consideration of hypoglycemia can result in a glucose risk value chart similar to that found in FIG. 4D where the glucose risk value approaches or is equal to zero around the tight glucose control range of 70-130 mg/dL. In still further embodiments, a log-normalized approach can be considered to generate a more evenly matched relative weights between hypoglycemia and hyperglycemia. FIGS. 4C and 4D further illustrate how conversion and normalization of risk metrics to risk values are customizable based on hospital protocols, physician preferences, or other considerations.

Figure 4E:
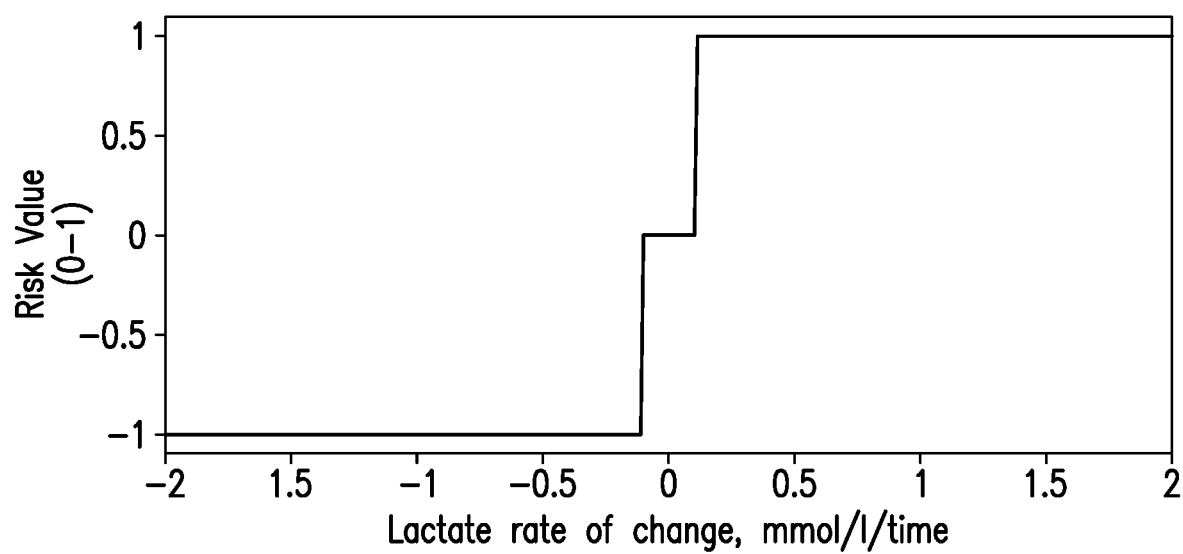
FIG. 4E is an exemplary chart of risk values associated with a secondary input, specifically, a rate of change of lactate, in accordance with embodiments of the invention.

FIG. 4E is an exemplary chart of risk values associated with a secondary input, specifically, a rate of change of lactate, in accordance with embodiments of the invention. As previously discussed, lactate trending data may be determined to support acute diagnosis or prediction of sepsis. Also previously discussed is decreasing lactate concentration being a signal of decreasing risk of sepsis and corresponding negative risk value.

FIG. 5 is an exemplary flowchart illustrating integration of the system within a therapy management system to enable a feedback mode in accordance with embodiments of the invention. Feedback mode is intended to monitor the effects of any treatment protocol and provide real-time, actionable information to external control algorithms whose aim is to optimize the management of therapy delivery to subjects with sepsis or a high risk of developing sepsis. This is accomplished by modifying therapy based on system output achieving targets and/or setpoints for specific risk metrics based on a specific clinical protocol. For example, if the clinical protocol is early goal directed therapy, feedback mode enables automatic or semi-automatic adjustments to the therapy based on the output of the system.

Operation 500 initiates feedback mode assuming the subject is already being monitored by the system and a decision has been made to initiate a therapy which is executed by operation 502. Various forms of therapy for sepsis include, but are not limited to fluid resuscitation or infusion of dobutamine. In a subsequent operation 504 data from the system, such as the risk score, along with real-time sensor values and rates of change in sensor values is gathered and used as input for the next operation. Later, operation 506 determines error in the input versus the targets and setpoints associated with the therapy. Operation 508 inputs the error from operation 506 into a controller that in operation 510 determines if changes to the therapy is needed. If augmentation to the therapy is recommended, in semi-automatic mode the system can notify a healthcare provided of suggested changes. In automatic mode, the system is enabled to make changes to therapy parameters such as infusion rates and the like. If the therapy protocol is within the targets or setpoints so no changes are recommended, operation 510 the flowchart returns to operation 504. The therapy management system described above incorporates a feedback loop. Other embodiments of the therapy management system can be further enhanced or improved with the addition of adaptive control. For example, in an embodiment employing adaptive control, if elevated lactate levels coincide with an increasing lactate clearance rate above a specified threshold, the risk score can be determined without taking into account the elevated lactate levels.

As previously discussed, the system is intended to be used in a variety of modes such as, but not limited to triage, monitoring, and remote monitoring each optionally supplemented by a feedback mode. Triage mode is intended to rapidly determine if a patient is afflicted with sepsis. The monitoring mode is intended to either monitor progress of a septic patient or provide notification if a patient is potentially developing sepsis. The remote monitor mode is intended to leverage mobile technology and cloud based communications to provide early notification of the potential development of sepsis in high-risk patients away from traditional medical or care facilities. The particular embodiments discussed above are exemplary embodiments of the system and should not be construed as the explicit limits of the system.

Other embodiments of the invention include separately or together, both detection and disease management based on continuous real time monitoring of multiple analytes indicative of disease states or medical conditions. For example, the system is adaptable to monitor the effectiveness of treatments such as, but not limited to chemotherapy. As many types of cancer are known to produce hyper metabolic activity within close proximity of a tumor, real time monitoring of metabolic activity near the tumor can provide insight of the efficacy of treatment. Similarly, the system is further adaptable to provide real time measurements and monitoring of analytes that are indicative of metabolic conditions and disease states associated therewith.

In addition to monitoring efficacy of cancer therapy and treatments, embodiments of the invention can also be used to monitor for conditions indicative of cancer in light of the following pathophysiological for some types of cancer. High energy metabolites such as ketones and lactate are associated with accelerated tumor growth and tumor metastases. Furthermore, increases in anabolic tumor growth rates are associated with upregulated mitochondrial metabolism which often are the byproduct of increases in circulating oxygen. Unique to behavior of cancer cells is the so called Warburg effect which describes the increased conversion to glucose to lactate even in the presence of normal to high levels of circulating oxygen. The energetically inefficient nature of the Warburg effect drives increases in glucose uptake through signaling pathways that ultimately leads to increases in insulin resistance and a concomitant increase in circulating glucose. The complex interplay amongst metabolic pathways associated with cancer cells suggest a continuous monitor capable of measuring ketones, oxygen, glucose, and lactate can be used to monitor those at risk for cancer, those who are being treated for cancer, and those who are at risk for cancer recurrence.

The continuous measurement of metabolites, their rates of change, and their relative concentrations can be analyzed through algorithms that serve to simulate or model the pathophysiological processes associated with tumor or cancer cell growth in order to identify individuals whose cancer risks have markedly increased and to then alert members of the care team through wired or wireless communication methods who can then initiate the appropriate intervention. A cancer monitoring system such as the one described above can also be used to monitor the effectiveness of a range of treatments and may in fact be used to enable more effective continuous treatment as opposed to the episodic or periodic protocols that tend to be reactive and as a result less effective in regards to treatment efficacy.

In embodiments not associated with metabolic conditions, the system is configurable to measure reactive oxide molecules such as, but not limited to nitric oxide and superoxide. As part of the body's inflammation response reactive oxide molecules are often overexpressed. Overexpression of reactive oxide molecules can cause the disruption of processes in the mitochondria and may have a role in mitochondrion dysfunction. Monitoring or detecting reactive oxide molecules and superoxide in relation to inflammation can be valuable within a hospital because of the strong indication for infection, regardless of patient profile.

While the description above refers to particular embodiments of the invention, it will be understood that many modifications may be made without departing from the spirit thereof. The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

The invention claimed is:

1. A system to enable risk assessment of the onset of sepsis, comprising:
   a sensor array for insertion within subcutaneous tissue for continuous monitoring of three analytes that are indicators of the onset of sepsis, the sensor array having an implantable portion that includes a plurality of electrodes;
   an electronics module having a power supply, a processor, a memory, and a bi-directional communications module, the electronics module configured to couple with the sensor array such that the power supply powers the sensor array and a processor is in communication with the sensor array, the processor calculating a risk score for the onset of sepsis based on characteristics of the three analytes being continuously monitored, the risk score being transmitted to and stored on a computer readable electronic health record, and
   a display,
   wherein the implantable portion is exposed to subcutaneous fluid when inserted within subcutaneous tissue,
   wherein the three analytes being continuously monitored are glucose, lactate and tissue oxygen,
   wherein the risk score is based upon real-time measurements of the three analytes,
   wherein calculating the risk score includes calculating a ratio of the concentrations of at least two of the three analytes, and
   wherein the risk score is displayed on the display.

2. The system of claim 1, wherein calculating the risk score further includes input from a physical condition sensor associated with the sensor array.

3. The system of claim 1, wherein calculating the risk score includes relative weighting factors assigned to each of the three analytes being measured, the relative weighting factors being stored in the memory of the electronics module.

4. The system of claim 1, wherein calculating the risk score further includes other data, the other data not being obtained by the sensor array.

5. The system of claim 1, wherein calculating the risk score includes rates of change of the real-time measurements of the three analytes.

6. The system of claim 5, wherein at least one of the rates of change of the three analytes is based on a different time period than the other rates of change.

7. The system of claim 6, wherein calculating the risk score includes relative weighting factors applied to the real-time measurements of the three analytes, the relative weighting factors being stored in the memory after being received via the bi-directional communications module.

8. The system of claim 6, wherein calculating the risk score includes at least one relative weighting factor based on a physical condition of a subject being monitored by the system, the at least one relative weighting factor being received via the bi-directional communications module and stored in the memory.

9. The system of claim 7, wherein at least one relative weighting factor of the relative weighting factors is automatically adjusted based on historical data.

10. The system of claim 8, wherein the at least one relative weighting factor is automatically adjusted based on historical data.

11. The system of claim 1 wherein the sensor array is introduced into subcutaneous tissue via a single point of entry.

12. An apparatus for early detection of sepsis in a host, comprising:
   an implantable portion that includes:
      a first sensor to directly measure a glucose level;
      a second sensor to directly measure a lactate level; and
      a third sensor to directly measure a tissue oxygen level;
      wherein the first sensor, the second sensor, and the third sensor are configured to be inserted at a single point of entry in a subcutaneous space of the host such that a predetermined correlation between the glucose level, lactate level, and tissue oxygen level signals conditions related to sepsis;
   an electronics module having a processor in communication with the implantable portion, the processor calculating a risk score for the onset of sepsis based on the glucose, lactate and tissue oxygen levels, the risk score being transmitted to and stored on a computer readable electronic health record; and a display, wherein the implantable portion is exposed to subcutaneous fluid when inserted within the subcutaneous space, wherein the risk score is based upon substantially real-time measurements from the first sensor, the second sensor and the third sensor, wherein calculating the risk score includes calculating the predetermined correlation, the predetermined correlation being a ratio of the concentrations of at least two of the glucose level, the lactate level and the tissue oxygen level, and wherein the risk score is displayed on the display.

13. The apparatus of claim 12, wherein the substantially real-time measurements of the first sensor, the second sensor and the third sensor are continuously taken at different intervals.

14. The apparatus of claim 13, wherein the different intervals are dynamically determined based on the substantially real-time measurements from at least one of the first sensor, the second sensor and the third sensor.

* * * * *